United States Patent [19]

Kalopissis et al.

[11] 4,248,591
[45] Feb. 3, 1981

[54] INDOANILINES, PROCESS FOR PRODUCING THE SAME AND KERATINIC FIBER DYE COMPOSITION CONTAINING THE SAME

[75] Inventors: Gregoire Kalopissis, Paris; Andree Bugaut, Boulogne-sur-Seine; Francoise Estradier, Paris, all of France

[73] Assignee: L'Oreal, Paris, France

[21] Appl. No.: 43,892

[22] Filed: May 30, 1979

Related U.S. Application Data

[62] Division of Ser. No. 691,216, May 28, 1976, which is a division of Ser. No. 482,494, Jun. 24, 1974, Pat. No. 3,977,825.

[30] Foreign Application Priority Data

Jun. 22, 1973 [LU] Luxembourg .............................. 67859

[51] Int. Cl.$^3$ .............................................. A61K 7/13
[52] U.S. Cl. ............................................ 132/7; 8/10;
8/10.2; 8/11; 8/416; 260/396 N
[58] Field of Search ................ 260/396 N; 8/10, 10.1, 8/10.2, 11

[56] References Cited
PUBLICATIONS

C.A., vol. 52, Hunig et al., 11054–11055 (1958).
Fieser et al., C.A., vol. 33, 2121 (1939).
C.A. 41: 2961h.
Vittum et al, J.A.C.S., vol. 68, pp. 2235–2239 (1946).
Vittum et al., J.A.C.S., vol. 69, pp. 152–155 (1947).

*Primary Examiner*—Allen J. Robinson
*Attorney, Agent, or Firm*—Cushman, Darby & Cushman

[57] ABSTRACT

Indoaniline of the formula

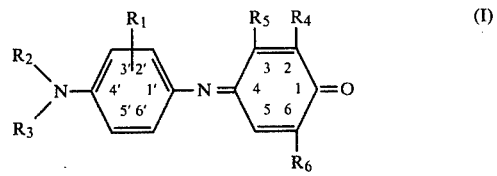

wherein $R_1$ represents hydrogen, halogen, alkyl or alkoxy; $R_2$ and $R_3$ represent alkyl; $R_4$, $R_5$ and $R_6$ each independently represent hydrogen, halogen, alkyl, alkoxy, acylamino, ureido or carbalkoxyamino and $R_5$ can also represent amino, alkylmaino, hydroxy alkylamino or carbamylalkylamino, the alkyl and alkoxy groups above being able to contain 1 to 6 carbon atoms and the acyl group from 2 to 7 carbon atoms with the condition that $R_5$ does not represent hydrogen, chlorine, methyl or methoxy and when $R_5$ represents acetylamino, $R_6$ does not represent hydrogen; it being understood that the above compounds can be present in the tautomeric form of that represented by formula (I). The indoaniline is usefully employed in dye copositions for keratinic fibers, especially living human hair.

9 Claims, No Drawings

INDOANILINES, PROCESS FOR PRODUCING THE SAME AND KERATINIC FIBER DYE COMPOSITION CONTAINING THE SAME

CROSS-REFERENCE TO PRIOR APPLICATIONS

This is a divisional application of U. S. application Ser. No. 691,216, filed May 28, 1976, which, in turn, is a divisional of U.S. application Ser. No. 482,494, filed Jun. 24, 1974, now U.S. Pat. No. 3,977,825.

The present invention relates to dialkylamine indoanilines of the formula

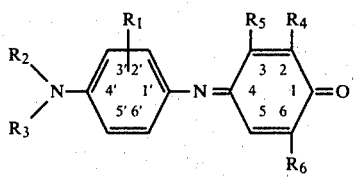

wherein $R_1$ represents hydrogen, halogen, alkyl or alkoxy; $R_2$ and $R_3$ represent alkyl, $R_4$, $R_5$ and $R_6$ each independently represents hydrogen, halogen, alkyl, alkoxy, acylamino, ureido or carbalkoxy amino, $R_5$ can also represent amino, alkylamino, hydroxyalkylamino or carbamylalkylamino, with the proviso that $R_5$ cannot represent hydrogen, chlorine, methyl or methoxy and when $R_5$ represents acetylamino, $R_6$ does not represent hydrogen (the above alkyl and alkoxy groups can contain from 1 to 6 carbon atoms and the acyl group can obtain from 2 to 7 carbon atoms). The present invention also relates to a process for preparing these compounds and to the preparation of dye compositions for keratinic fibers and in particular for living human hair containing said compounds. It will be appreciated that the above compounds can be present under tautomeric forms of that which is represented by formula (I).

Amond the tautomer forms possible, one can cite the formula

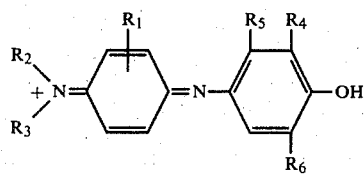

and when $R_5$ designates an amino, alkylamino, hydroxyalkylamino, or carbamylalklamino, the formula

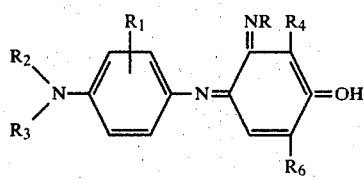

wherein $R_1$ to $R_6$ have the meanings given above and R represents hydrogen, alkyl, hydroxyalkyl, or carbamylalkyl.

The compounds of formula (I) can be prepared by condensing a compound of the formula

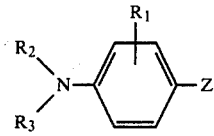

wherein Z represents $NH_2$, or NO when $R_1$ is in meta position relative to the $-NR_2R_3$ group, on a phenolic compound of the formula

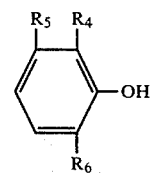

wherein $R_1$, $R_2$, $R_3$, $R_4$, $R_5$ and $R_6$ have the meanings given above, or the meanings given on page 7.

In a first method of preparation, when Z represents $NH_2$, one condenses the phenolic compound of formula (III) on a paraphenylenediamine of the formula

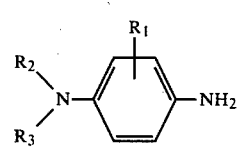

wherein $R_1$, $R_2$ and $R_3$ have the meanings given above in an aqueous alkaline medium, in a hydroalcoholic medium, preferably hydroethanolic or hydroisopropanolic or in a hydroacetonic medium having a pH greater than 8 in the presence of an oxidizing agent and at a temperature of about 0° C.

The ratio of the phenolic compound to the paraphenylenediamine is between about 1:1 and 2:2, this ratio generally being about 1:1.

The oxidizing agent usefully employed in this condensation reaction can be, for example, $H_2O_2$, an alkaline persulfate, for example, the persulfate of potassium or ammonium, an alkaline ferricyanide, for example potassium ferricyanide. The quantity of the oxidizing agent employed can vary from 1-5 times preferably 1-3 times the stoichiometric amount required for oxidizing the p-phenylenediamine to a quinone diimine.

As phenols, one can use 2-methyl-5-ureido phenol, 2-methyl-5-acetylamino phenol, 2-methyl-5-amino phenol, 2-methyl-5-methylamino phenol, 3-ureido phenol, 2,6-dimethyl-5-acetylamino phenol, 2,6-dimethyl-3-amino phenol, 2,6-xylenol, 2-acetylamino phenol, meta-aminophenol, 2,6-dimethyl-3-ureido phenol, 3-methoxy phenol, 3-acetylamino phenol, 2-methyl-5-carbamylmethylaminophenol, 2,6-dimethyl phenol, 2-methyl-5-carbethoxyamino phenol, 2,6-dimethyl-5-amino phenol, 2-methyl-5(N-β-hydroxyethylamino) phenol, 2,5-dimethyl phenol, 2,3-xylenol, 2-ureido phenol, 2-chloro-5-amino phenol, 2-chloro-5-acetylamino phenol and 3-chloro-6-acetylamino phenol.

As the paraphenylenediamines one can use, for instance, N,N-dimethyl paraphenylenediamine, 2-methyl-4-N,N-diethylamino aniline, 4-N,N-diethylamino-2-chloroaniline, 3-methoxy-4-amino-N,N-dimethyl aniline, 3-chloro-4-amino-N,N-dimethyl aniline, 3-methyl-4-amino-dimethyl aniline, N,N-diethyl-p-phenylenediamine, 4-N,N-diethylamino-3-chloroaniline, 4-N,N- dimethylamino-3-chloroaniline and N,N-dibutyl-p-phenylenediamine.

The paraphenylenediamines can be replaced by one of their salts and in particular by the hydrochloride, hydrobromide, sulfate or phosphate thereof.

In a second method of the present invention, when Z represents NO, one condenses the phenolic compound of formula (III) on a nitroso derivative of formula (V)

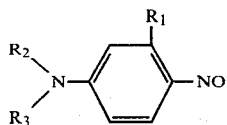

wherein $R_1$, $R_2$ and $R_3$ have the meanings given above. This condensation reaction is effected in an aqueous or hydroalcoholic medium preferably a hydroethanolic or a hydroisopropanolic medium at a temperature between about 30° and 60° C., and preferably between 40° and 55° C.

Representative nitroso compounds that can usefully be employed include, 4-nitroso-N,N-dibutylaniline, 3-chloro-4-nitroso diethylaniline and 3-methoxy-4-nitroso-N,N-dimethylaniline.

The compounds wherein $R_1$ is in a position ortho relative to the —$NR_2R_3$ group and $R_5$ is amino can be obtained by hydrolysis using a base such as NaOH on the corresponding 3-acetylated derivative.

The indoanilines of formula (I), wherein $R_1$ represents hydrogen, halogne, alkyl or alkoxy; $R_2$ and $R_3$ represent alkyl; $R_4$, $R_5$ and $R_6$ each independently represents hydrogen, halogen, alkyl, alkoxy, acylamino, ureido, or carbalkoxyamino and $R_5$ can also designate amino, alkylamino, hydroxy-alkylamino or carbamylalkylamino (the above alkyl groups being able to contain 1to 6 carbon atoms) with the proviso that $R_5$ does not represent hydrogen, chlorine, methoxy or methyl and when $R_5$ represents acetylamino, $R_6$ does not represent hydrogen, are new compounds.

Additionally, the following are new compounds:
N-[(4'-diethylamino-2'-methyl)phenyl]-2,6-dimethyl benzoquinoneimine,
N-[(4'-diethylamino-2'-chloro)phenyl]-2-acetamino benzoquinoneimine,
N-[(4'-dimethylamino-2'-methyl)phenyl]-2,6-dimethyl benzoquinoneimine,
N-[((4'-dimethylamino-2'-chloro)phenyl]-2,6-dimethyl benzoquinoneimine,
N-[(4'-dimethylamino-2'-methoxy)phenyl]-2,6-dimethyl benzoquinoneimine, and
N-[(4'-dimethylamino-3'-chloro)phenyl]- 2,6-dimethyl-benzoquinoneimine.

The present invention also has for an object the dyes obtained by the condensation of a compound of formula (II) on a compound of formula (III), as well as dyes obtained by the hydrolysis of a compound acetylated in position 3 in the corresponding aminated dye.

The dyes find an interesting application in the dyeing of keratinic fibers and in particular of living human hair.

The present invention also has for an object a dye composition for keratinic fibers, in particular for living human hair, characterized by the fact that they include in an aqueous or hydroalcoholic solution, at least one compound of formula (I)

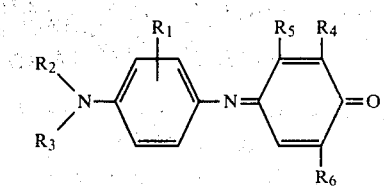

wherein $R_1$ represents hydrogen, halogen, alkyl or alkoxy; $R_2$ and $R_3$ each independently represents alkyl; $R_4$, $R_5$ and $R_6$ each independently represent hydrogen, halogen, alkyl, alkoxy, acylamino, ureido, or carbalkoxyamino and $R_5$ can also represent amino, alkylamino, hydroxyalkylamino or carbamylalkylamino; it being understood that the alkyl groups can contain from 1 to 6 carbon atoms and the acyl groups can contain from 2 to 7 carbon atoms.

These dye compositions include from 0.0075 to 2% and preferably from 0.02 to 0.5% of the compound of formula (I) of the total weight of the composition.

The dye compositions according to the present invention can include only the indoanilines of formula (I).

It is, however, possible to mix the dyes according to the invention with other dyes conventionally utilized for the dyeing of hair, for example nitro benzene dyes, azo dyes, anthraquinone dyes, indamines, indophenols and/or other indoanilines.

The compositions according to the present invention are generally present in the form of an aqueous or hydroalcoholic solution containing one or more compounds of formula (I), in mixture or not with other dyes. They can, however, also include thickening agents and be present in the form of creams or gels.

To illustrate thickening agents that can be incorporated in the dye compostions of the present invention, one can mention cellulose derivatives such a methylcellulose, hydroxyethylcellulose, carboxymethylcellulose or acrylic polymers such as the sodium salt of polyacrylic acid or carboxyvinyl polymers.

The dye compositions can include as solvents, water, lower alkanols, such as ethanol or isopropanol, polyalcohols such as glycols, for example, ethyleneglycol, propyleneglycol, butylglycol, diethyleneglycol and the monomethylether of diethyleneglycol.

The compositions according to the invention can also include various components conventionally utilized in cosmetic preparations, such as wetting agents, for example, oxyethylenated alkyl phenols, oxyethylenated fatty acids, oxyethylenated fatty alcohols, the sulfates and sulfonates of fatty alcohols optionally oxyethylenated, dispersing agents, swelling agents, penetrating agents, emollients, polymers and/or perfumes. They can also be packaged in aerosol containers under pressure in the presence of a gaseous propellent.

One can use as the gaseous propellent, nitrogen, nitrous oxide, volatile hydrocarbons such as butane, isobutane, propane or preferably the fluoronated hydrocarbons sold under the name of FREON by Dupont, such a dichlorodifluoromethane, 1,1-difluoromethane, 1,2-dichloro-(1,1,2,2-tetrafluoromethane) or 1-chloro-1,1-difluoromethane; a mixture of two or more hydrocarbons or fluoronated hydrocarbons can also be utilized.

The pH of the compositions can vary to a large extent. It is generally between about 4 to 11 and preferably between 6.5 and 10.5 and advantageously between 7 and 9.

One can adjust the pH of the composition with an alkalizing agent for example, ammonia, mono-, di- or triethanolamine, trisodium or disodium phosphate, sodium or potassium carbonate or with an acidifying agent for example, acetic acid, lactic acid, phosphoric acid, or citric acid.

The dyeing of keratinic fibers, in particular, living human hair, with the dye compositions according to the present invention can be effected in a conventional manner by applying the composition to the fibers to be dyed, permitting said composition to remain in contact therewith for a period varying from 5 to 30 minutes, followed by rinsing and eventually washing and drying the fibers.

The compositions according to the invention, when present in the form of a hydroalcoholic solution, can also include a cosmetic film-forming resin and thus constitute a colored hair setting lotion which can be applied to wet hair before the hair is set.

Representative cosmetic resins that can be employed in these hair setting lotion compositions include polyvinyl pyrrolidone; copolymers of polyvinylpyrrolidone and vinyl acetate; copolymers of vinyl acetate and an unsaturated carboxylic acid, such as crotonic acid; copolymers resulting from the copolymerization of vinyl acetate, crotonic acid and an acrylic or methacrylic ester; copolymers resulting from the copolymerization of vinyl acetate and a vinyl alkyl ether; copolymers resulting from the copolymerization of vinyl acetate, crotonic acid and a vinyl ester of a long carbon chain acid or an acrylic or methacrylic ester of a long carbon chain acid; copolymers resulting from the copolymerization of an ester derived from an unsaturated alcohol and short carbon chain acid, from an unsaturated acid having a short carbon chain, and from at least one ester derived from an unsaturated short chain alcohol and an unsaturated acid; and copolymers resulting from the copolymerization of at least one unsaturated ester and at least one unsaturated acid.

Representative preferred resins include polyvinylpyrrolidone having a molecular weight from 10,000 to 160,000; copolymers of 10% crotonic acid and 90% vinyl acetate having a molecular weight from 10,000 to 70,000; copolymers of polyvinylpyrrolidone (PVP) and vinyl acetate (VA) having a molecular weight of 30,000 to 200,000, the ratio of PVP to VA being between about 30:70 and 70:30; copolymers of maleic anhydride and methylvinyl ether having a molar ratio of 1:1 and a specific viscosity, measured at 25° C. at a concentration of 1 gram in 100 cc of methylethyl ketone, between 0.1 and 3.5; the monoethyl ester, monoisopropyl ester and monobutyl ester of these copolymers of maleic anhydride and methylvinyl ether; the copolymer of maleic anhydride and of butylvinyl ether having a mole ratio of 1:1; the terpolymers of methylmethacrylate (15 to 25%)—stearylmethacrylate (18 to 28%) and dimethylmethacrylate (52 to 62%); and the terpolymers of vinyl acetate (75 to 85%)—allylstearate (10 to 20%) and allyloxyacetic acid (3 to 10%).

These resins are used generally in amounts between about 1 to 3% by weight of the total composition.

The alcohols employed to produce the hair setting lotions according to the present invention are low molecular weight alcohols and preferably are ethanol or isopropanol. These alcohols are generally used in amounts of about 20 to 70% by weight of the total composition.

The hair setting lotions according to the present invention can be employed in a conventional manner by applying the same to living human hair previously washed and rinsed, followed by rolling the same on rollers and then drying the hair.

The invention is illustrated by the following examples:

EXAMPLE I

Preparation of N-[(4'-dimethylamino)phenyl]-2-methyl-5-ureido benzoquinoneimine.

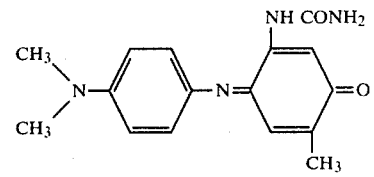

0.1 mole (16.6 grams) of 2-methyl-5-ureido phenol is dissolved in 400 cc of isopropyl alcohol to which have been added 400 cc of ammonia at 22° Bé. To this solution, there is added 0.1 mole (20.9 grams) of the dihydrochloride of N,N-dimethyl paraphenylenediamine in 650 cc of water. After adding to this mixture 800 g of crushed ice, there is introduced, little by little, with good agitation and while maintaining the temperature near 0° C., 0.2 mole (45.6 g) of ammonium persulfate in 150 cc of water. At the end of this addition, the above indoaniline which has precipitated is filtered, washed with water, recrystallized in a mixture of dimethylformamide and water and dried under a vacuum. It exhibits a melting point of 275° C.

| Analysis | Calculated For $C_{16}H_{18}N_4O_2$ | Found | |
|---|---|---|---|
| C% | 64.41 | 64.29 | 64.44 |
| H% | 6.37 | 6.31 | 6.26 |
| N% | 18.78 | 19.01 | 18.93 |

EXAMPLE II

Preparation of N-[(4'-dimethylamino)phenyl]-2-methyl-5-acetylamino benzoquinoneimine.

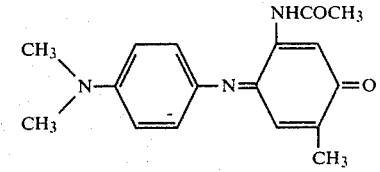

0.16 mole (26.4 g) of 2-methyl-5-acetyl-amino phenol is dissolved in 700 cc of isopropanol to which have been added 800 cc of ammonia at 22° Bé. To this solution, there is added 0.176 mole (36.8 g) of the dihydrochloride of N,N-dimethylparaphenylenediamine in 100 cc of water and 1.3 kg of crushed ice. There is then added to the resulting mixture, whose temperature is maintained at about 0° C. little by little, and with agitation, 0.352 moles (80.25 g) of ammonium persulfate in 200 cc of water. At the end of this addition the above indoaniline which has precipitated is filtered, washed with water and recrystallized in a mixture of dimethylformamide and water. The above product exhibits a melting point of 180° C.

| Analysis | Calculated For $C_{17}H_{19}O_2N_3$ | Found |
|---|---|---|
| C% | 68.72 | 68.59 |
| H% | 6.39 | 6.59 |
| N% | 14.14 | 13.96 |

EXAMPLE III

Preparation of N-[(4'-dimethylamino)phenyl]-2-methyl-5-amino benzoquinoneimine.

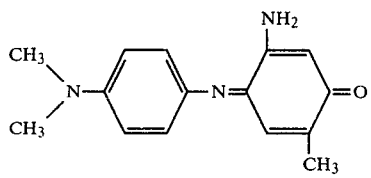

0.2 mole (24.6 g) of 2-methyl-5-amino phenol is dissolved in 500 cc of acetone to which have been added 200 cc of water and 500 cc of ammonia at 22° Bé. There are then added 500 g of crushed ice. Little by little and with agitation, there are introduced into this reaction mixture, maintained at about 5° C. simultaneously with the aid of a double funnel, 0.2 mole (41.8 g) of the dihydrochloride of N,N-dimethyl paraphenylenediamine in 320 cc of water and 0.2 mole (45.8 g) of ammonium persulfate in 200 cc of water. At the end of this addition, the above indoaniline, which has precipitated, is filtered, washed with water, recrystallized in a mixture of dimethylformamide and water and dried under a vacuum. It exhibits a melting point of 255° C.

| Analysis | Calculated For $C_{15}H_{17}ON_3$ | Found |
|---|---|---|
| C% | 70.58 | 70.45 |
| H% | 6.66 | 6.82 |
| N% | 16.47 | 16.34 |

EXAMPLE IV

Preparation of N-[(4'-dimethylamino)phenyl]-2-methyl-5-methylamino benzoquinoneimine.

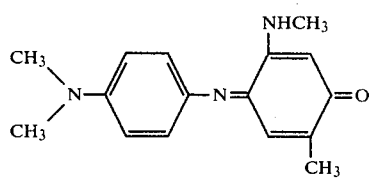

0.025 mole (3.42 g) of 2-methyl-5-methylamino phenol is dissolved in 100 cc of water to which have been added 100 cc of ammonia at 22° Bé. 150 g of crushed ice are then added to this solution. The resulting reaction mixture is maintained at a temperature of about 5° C. There are then introduced simultaneously, with good agitation and with the aid of a double funnel, 0.025 mole (5.23 g) of the dihydrochloride of N,N-dimethyl paraphenylenediamine in 50 cc of water and 0.025 mole (5.7 g) of ammonium persulfate in 50 cc of water. The above indoaniline which has precipitated is then filtered, washed with water and recrystallized in a mixture of dimethylformamide and water. After drying under a vacuum, it exhibits a melting point of 202° C.

| Analysis | Calculated For $C_{16}H_{19}N_3O$ | Found | |
|---|---|---|---|
| C% | 71.34 | 71.23 | 71.19 |
| H% | 7.11 | 7.01 | 7.01 |
| N% | 15.60 | 15.61 | 15.73 |

EXAMPLE V

Preparation of N-[(4'-dimethylamino phenyl]-3-ureido benzoquinoneimine.

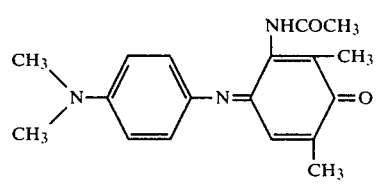

0.03 mole (4.56 g) of 3-ureido phenol is dissolved in 100 cc of isopropyl alcohol to which have been added 100 cc of ammonia at 22° Bé. 350 g of crushed ice are then added to this solution. The resulting reaction mixture is maintained at about 0° C., and there are introduced simultaneously, with good agitation and with the aid of a double funnel, 0.03 mole (6.27 g) of the dihydrochloride of N,N-dimethyl paraphenylenediamine in 50 cc of water and 0.060 mole (13.7 g) of ammonium persulfate in 50 cc of water. At the end of this addition, the agitation is continued for 15 minutes and the above indoaniline which has precipitated is then filtered, washed with water, recrystallized in a mixture of dimethylformamide in water and dried under a vacuum. It exhibits a melting point of 226° C.

| Analysis | Calculated For $C_{15}H_{16}N_4O_2$ | Found | |
|---|---|---|---|
| C% | 63.36 | 63.45 | 63.52 |
| H% | 5.67 | 5.77 | 5.83 |
| N% | 19.71 | 19.88 | 19.72 |

EXAMPLE VI

Preparation of N-[(4'-dimethylamino)phenyl]-2,6-dimethyl-3-acetylamino benzoquinoneimine.

0.3 mole (53.7 g) of 2,6-dimethyl-3-acetylamino phenol is dissolved in 400 cc of acetone to which have been added 400 cc of ammonia at 22° Bé. The resulting mixture is maintained at a temperature of about 10° C., and there are introduced therein simultaneously, with the aid of a double funnel, 0.3 mole (62.7 g) of the dihydrochloride of N,N-dimethyl paraphenylenediamine in 500 cc of water and 0.6 mole (137 g) of ammonium persulfate in 500 cc of water. The above indoaniline which precipitates is then filtered, washed with water, recrystallized in a mixture of dimethylformamide and water and dried under a vacuum. It exhibits a melting point of 111° C.

| Analysis | Calculated For $C_{18}H_{21}O_2N_3$ | Found | |
|---|---|---|---|
| C% | 69.43 | 69.13 | 69.25 |
| H% | 6.80 | 6.64 | 6.74 |
| N% | 13.50 | 13.72 | 13.60 |

EXAMPLE VII

Preparation of N-[(4'-dimethylamino)phenyl]-2,6-dimethyl-3-amino benzoquinoneimine.

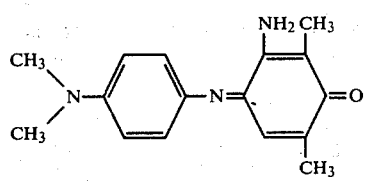

0.4 mole (69.4 g) of 2,6-dimethyl-3-amino phenol is dissolved in 1 liter of acetone to which has been added 1 liter of ammonia at 22° Bé. 1 kg of crushed ice is then added to this solution and then with the aid of a double funnel, there are introduced simultaneously, with good agitation, 0.4 mole (83.6 g) of the dihydrochloride of N,N-dimethylparaphenylenediamine in 1 liter of water and 0.44 mole (100 g) of ammonium persulfate in 800 cc of water. The temperature of the reaction mixture is maintained at about 0° C. At the end of the addition, the raw product is filtered, washed with water and recrystallized in a mixture of dimethylformamide and water. After drying under a vacuum, the above indoaniline exhibits a melting point of 178° C.

| Analysis | Calculated For $C_{16}H_{19}ON_3$ | Found | |
|---|---|---|---|
| C% | 71.34 | 71.41 | 71.57 |
| H% | 7.11 | 7.19 | 7.26 |
| N% | 15.60 | 15.45 | 15.57 |

EXAMPLE VIII

Preparation of N-[(4'-diethylamino-2'-methyl) phenyl]-2,6-dimethyl benzoquinoneimine.

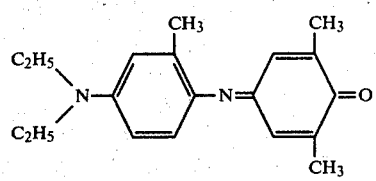

0.01 mole (2.51 g) of the dihydrochloride of 2-methyl-4-N,N-diethylamino aniline and 0.01 mole (1.22 g) of 2,6-xylenol are dissolved in 85 cc of normal sodium hydroxide solution to which have been added 20 cc of ethanol. Little by little, to this solution, with agitation and while maintaining the temperature near about 0° C., there is added 0.02 mole (4.56 g) of ammonium persulfate in 46 cc of water. The raw indoaniline above is filtered, washed with water and recrystallized in a mixture of water and acetone. After drying under a vacuum, the product exhibits a melting point of 128° C.

| Analysis | Calculated For $C_{19}H_{24}N_2O$ | Found | |
|---|---|---|---|
| C% | 76.99 | 76.83 | 76.76 |
| H% | 8.16 | 8.05 | 8.19 |
| N% | 9.45 | 9.32 | 9.54 |

EXAMPLE IX

Preparation of N-[(4'-diethylamino-2'-chloro) phenyl]-2-acetamino benzoquinoneimine.

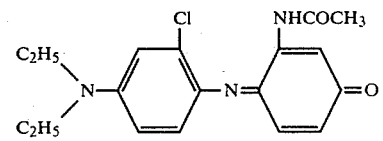

0.01 mole (1.51 g) of 2-acetylamino phenol is dissolved in 25 cc of isopropyl alcohol to which have been added 25 cc of ammonia at 22 Bé. There are then added 50 g of crushed ice. The resulting mixture is maintained at a temperature of about 0° C., and there are then introduced simultaneously with agitation, 0.01, mole (2.71 g) of the dihydrochloride of 2-chloro-4-N,N-diethylamino aniline in 20 cc of water and 0.02 mole (4.46 g) of ammonium persulfate in 25 cc of water. At the end of this addition, the above indoaniline which precipitates is filtered, washed with water, recrystallized in dimethylformamide, and dried under a vacuum. The product exhibits a melting point of 155° C.

| Analysis | Calculated For $C_{18}H_{20}N_3ClO_2$ | Found | |
|---|---|---|---|
| C% | 62.51 | 62.76 | 62.75 |
| H% | 5.80 | 5.95 | 5.95 |
| N% | 12.18 | 12.16 | 12.32 |

EXAMPLE X

Preparation of N-[(4'-dimethylamino) phenyl]-3-amino benzoquinoneimine.

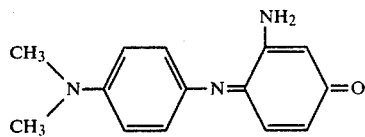

0.01 mole (2.09 g) of the dihydrochloride of N,N-dimethylparaphenylenediamine and, 0.01 mole (1.09 g) of metaaminophenol are dissolved in 40 cc of water to which have been added 7 cc of ammonia at 22° Bé. To this solution, cooled to 0° C., there are added 20 cc of $H_2O_2$ (20 volumes). The resulting reaction mixture is left to stand for 24 hours at ambient temperature. The raw product which has precipitated is then filtered, washed with water and dried under a vacuum. This raw product is then extracted 4 times with 100 cc of ether, at 20° C. The etherified extracts are then combined and concentrated under a vacuum to a volume of about 10 cc. After cooling, the above indoaniline which has crystallized is filtered, recrystallized in dimethylformamide and dried under a vacuum. The product exhibits a melting point of 171° C., and is chromatographically pure. Molecular mass calculated for $C_{14}H_{15}N_3O$:241. Molecular mass found by potentiometric dosage effected in methylisobutylketone with perchloric acid: 240.

| Analysis | Calculated For $C_{14}H_{15}N_3O$ | Found | |
|---|---|---|---|
| C% | 69.69 | 69.58 | 69.46 |
| H% | 6.27 | 6.26 | 6.27 |
| N% | 17.42 | 17.70 | 17.64 |

EXAMPLE XI

Preparation of N-[(4'-dimethylamino) phenyl]-2,6-dimethyl-5-ureido benzoquinoneimine.

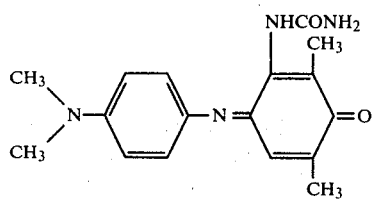

0.2 mole (36 g) of 2,6-dimethyl-3-ureido phenol is dissolved in 1 liter of isopropyl alcohol to which have been added 800 cc of ammonia at 22° Bé. There are then added 800 g of crushed ice to this reaction mixture. Then, little by little and with good agitation, there are introduced simultaneously, 0.2 mole (41 g) of the dihydrochloride of N,N-dimethylparaphenylenediamine in 500 cc of water and 0.4 mole (92 g) of ammonium persulfate in 500 cc of water. During the time of these additions, the temperature of the reaction mixture is maintained at about 0° C. At the end of these additions, the above indoaniline is filtered, washed with water and dried under a vacuum. The product is chromatographically pure and melts at a temperature of 245° C.

| Analysis | Calculated For $C_{17}H_{20}N_4O_2$ | Found | |
|---|---|---|---|
| C% | 65.36 | 65.60 | 65.61 |
| H% | 6.45 | 6.55 | 6.57 |
| N% | 17.94 | 18.08 | 17.97 |

EXAMPLE XII

Preparation of N-[(4'-dibutylamino) phenyl]-2-methyl-5-carbamylmethylamino benzoquinoneimine.

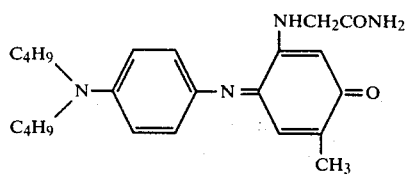

0.01 mole (2.7 g) of the hydrochloride of 4-nitroso-N,N-dibutylaniline and 0.01 mole (1.80 g) of 2-methyl-5-carbamylmethylamino phenol are dissolved in 30 cc of a 50% hydroethanolic solution. The resulting reaction mixture is stirred for a period of 1 hour at 40° C. The above raw indoaniline which has precipitated is then filtered and dissolved in 10 cc of dimethylformamide at ambient temperature. After filtration, in order to eliminate secondary insoluble products formed in a minor quantity, there are added 10 ml of water to reprecipitate the indoaniline which is then filtered, washed with water and dried under a vacuum. The product is chromatographically pure and melts at 169° C.

| Analysis | Calculated For $C_{23}H_{32}N_4O_2$ | Found | |
|---|---|---|---|
| C% | 69.66 | 69.80 | 69.68 |
| H% | 8.13 | 8.23 | 8.26 |
| N% | 14.13 | 14.04 | 13.98 |

EXAMPLE XIII

Preparation of N-[(4'-diethylamino-2'-chloro) phenyl]-2,6-dimethyl-3-amino benzoquinoneimine.

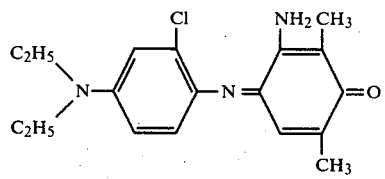

Into 30 cc of ethanol to which have been added 20 cc of a normal sodium hydroxide solution, there are introduced 0.01 mole (2.12 g) of 3-chloro-4-nitroso diethylaniline and 0.011 mole (1.91 g) of the hydrochloride of 2,6-dimethyl-3-amino phenol. The mixture is maintained with agitation for 4 hours at 35° C. The above indoaniline is then filtered, washed several times with water at 50° C., and recrystallized in a mixture of dimethylformamide in water. The product exhibits a melting point of 160° C.

| Analysis | Calculated For $C_{18}H_{22}N_3ClO$ | Found | |
|---|---|---|---|
| C% | 65.15 | 65.04 | 65.14 |
| H% | 6.65 | 6.72 | 6.74 |
| N% | 12.67 | 12.73 | 12.69 |
| Cl% | 10.70 | 10.84 | 10.92 |

EXAMPLE XIV

Preparation of N-[(4'-dimethylamino) phenyl]-2-chloro-5-amino benzoquinoneimine.

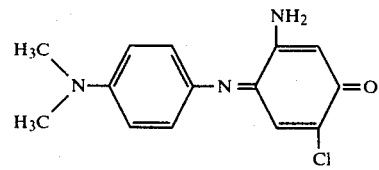

0.01 mole (2.09 g) of the dihydrochloride of N,N-dimethylparaphenylenediamine and 0.01 mole (1.43 g) of 2-chloro-5-amino phenol are dissolved in 150 cc of a 0.7 N sodium hydroxide solution. To this solution, cooled to 0° C., there is added, little by little, with agitation, 0.02 mole (4.60 g) of ammonium persulfate in solution in 20 cc of water. At the end of this addition, the agitation of the mixture is continued for an additional 15 minutes. The above indoaniline which precipitates is filtered, washed with water and then with acetone. The raw product is dissolved in dimethylformamide at 0° C., (10 cc of dimethylformamide per gram of raw product). The resulting solution is then filtered to eliminate a slightly insoluble white product. After cooling the filtrate to 0° C., the above indoaniline crystallizes in the form of reddish-brown flakes having golden glints. These flakes are filtered and dried under a vacuum. After drying, the product exhibits a melting point of 242° C.

| Analysis | Calculated For $C_{14}H_{14}N_3ClO$ | Found | |
|---|---|---|---|
| C% | 60.98 | 61.09 | 60.92 |
| H% | 5.09 | 5.00 | 4.96 |
| N% | 15.24 | 15.40 | 15.21 |
| Cl% | 12.87 | 12.93 | 13.02 |

EXAMPLE XV

Preparation of N-[(4'-dimethylamino-2'-methyl)phenyl]-2,6-dimethyl benzoquinoneimine.

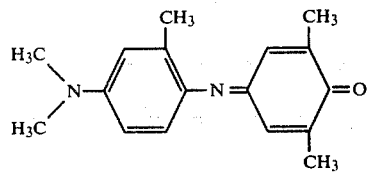

0.01 mole (1.22 g) of 2,6-dimethyl phenol is dissolved in 20 cc of acetone, 5 cc of water and 15 cc of ammonia (22° Bé). To this solution, maintained at a temperature of about +5° C., there are added, little by little, with agitation, and simultaneously with the aid of a double funnel, 0.01 mole (2.23 g) of the dihydrocloride of 3-methyl-4-amino-N,N-dimethylaniline dissolved in 15 cc of water and 0.02 mole (4.6 g) of ammonium persulfate dissolved in 20 cc of water. At the end of these additions, the stirring of the reaction mixture is continued for one hour at ambient temperature. The above indoaniline which has precipitated is then filtered, washed with water, recrystallized in a mixture of dimethylformamide and water and dried under a vacuum. It exhibits a melting point of 157° C.

| Analysis | Calculated For $C_{17}H_{20}N_2O$ | Found |
|---|---|---|
| C% | 76.08 | 75.95 |
| H% | 7.51 | 7.51 |
| N% | 10.44 | 10.46 |

EXAMPLE XVI

Preparation of N-[(4'-dimethylamino-2'-chloro)phenyl]-2,6-dimethyl benzoquinoneimine.

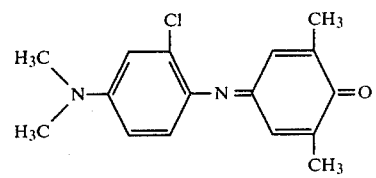

0.01 mole (1.22 g) of 2,6-dimethyl phenol and 0.01 mole (2.44 g) of the dihydrochloride of 3-chloro-4-amino-N,N-dimethylaniline are dissolved in 20 cc of acetone, 15 cc of water and 15 cc of ammonia (22° Bé). To this resulting solution, cooled to about +5° C., there is added, little by little, with agitation, 0.02 mole of ammonium persulfate dissolved in 20 cc of water. At the end of this addition, the stirring is continued for 30 minutes. The above indoaniline which has precipitated is filtered, washed with water and dried under a vacuum. It exhibits a melting point of 154° C.

| Analysis | Calculated For $C_{16}H_{17}ClN_2O$ | Found |
|---|---|---|
| C% | 66.19 | 66.04 |
| H% | 5.58 | 5.80 |
| N% | 9.70 | 9.74 |
| Cl% | 12.27 | 12.14 |

EXAMPLE XVII

Preparation of N-[(4'-dimethylamino-2'-methoxy)phenyl]-2,6dimethyl benzoquinoneimine.

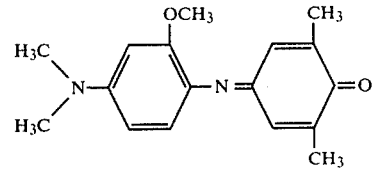

0.01 mole (2.64 g) of 3-methoxy-4-amino-N,N-dimethylaniline sulfate and 0.01 mole (1.22 g) of 2,6-dimethyl phenol are dissolved in 20 cc of water, 35 cc of acetone and 10 cc of ammonia (22° Bé). To the resulting solution, cooled in ice, there is added, little by little, with agitation, 0.02 mole (4.6 g) of ammonium persulfate in 20 cc of water. At the end of this addition the stirring of the reaction mixture is continued for one hour. The above indoaniline which has precipitated is then filtered, washed first with water and then with acetone and dried under a vacuum. It exhibits a melting point of 140° C.

| Analysis | Calculated For $C_{17}H_{20}N_2O_2$ | Found |
|---|---|---|
| C% | 71.80 | 71.60 |
| H% | 7.09 | 7.06 |
| N% | 9.85 | 9.99 |

EXAMPLE XVIII

Preparation of
N-[(4'-dimethylamino-2'-methyl)phenyl]-6-methyl-3-amino benzoquinoneimine.

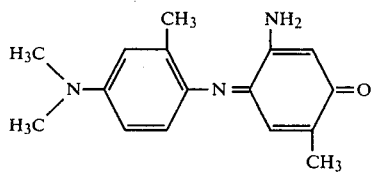

0.02 mole (2.46 g) of 2-methyl-5-amino phenol is dissolved in 40 cc of acetone, 10 cc of ice and 30 cc of ammonia (22° Bé). To the resulting solution, maintained at a temperature of about +5° C., there are added, little by little, with agitation and simultaneously with the aid of a double funnel, 0.02 mole (4.46 g) of the dihydrochloride of 3-methyl-4-amino-N,N-dimethylaniline dissolved in 25 cc of water and 0.02 mole (4.6 g) of ammonium persulfate dissolved in 10 cc of water. At the end of this addition, the stirring of the reaction mixture is continued for one hour at ambient temperature. The above indoaniline which has precipitated is then filtered, washed with water, recrystallized in a mixture of dimethylformamide and water and dried under a vacuum. It exhibits a melting point of 200° C.

| Analysis | Calculated For $C_{16}H_{19}N_3O$ | Found |
|---|---|---|
| C% | 71.34 | 71.41 |
| H% | 7.11 | 7.37 |
| N% | 15.60 | 15.79 |

EXAMPLE XIX

Preparation of
N-[(4'-dimethylamino-2'-methoxy-)phenyl]-6-methyl-3-amino benzoquinoneimine.

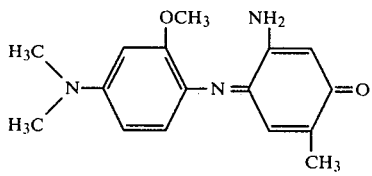

0.012 mole (3.2 g) of 3-methoxy-4-amino-N,N-dimethylaniline sulfate and 0.02 mole (2.46 g) of 2-methyl-5-amino phenol are dissolved in 60 cc of a 50% hydroacetonic solution to which have been added 20 cc of ammonia (22° Bé). To the resulting solution, maintained at a temperature of about 0° C., there is added, little by little, with agitation, 0.02 mole (4.6 g) of ammonium persulfate dissolved in 20 cc of water. At the end of this addition, stirring of the reaction mixture is continued for one hour at 0° C. The above indoaniline which has precipitated is then filtered, washed first with water and then with a normal NaOH solution to eliminate the 2-methyl-5-amino phenol that it contains, and finally with water. After recrystallization in a mixture of dimethylformamide and water and drying under a vacuum, the product exhibits a melting point of 168° C.

| Analysis | Calculated For $C_{16}H_{19}N_3O_2$ | Found |
|---|---|---|
| C% | 67.34 | 67.32 |
| H% | 6.71 | 6.77 |
| N% | 14.73 | 14.58 |

EXAMPLE XX

Preparation of N-[(4'-dimethylamino-2'-chloro) phenyl]-6-methyl-3-acetylamino benzoquinoneimine.

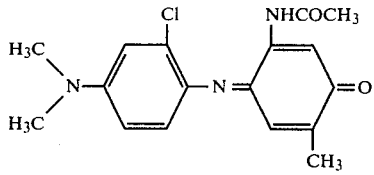

0.01 mole (1.65 g) of 2-methyl-5-acetylamino phenol and 0.01 mole (2.44 g) of the dihydrochloride of 3-chloro-4-amino-N,N-dimethylaniline are dissolved in 20 cc of acetone to which have been added 15 cc of water and 15 cc of ammonia (22° Bé). To the resulting solution, maintained at a temperature of about +5° C., there is added, little by little, with agitation, 0.02 mole (4.6 g) of ammonium persulfate in 20 cc of water. At the end of this addition, the stirring of the reaction mixture is continued for 30 minutes. The above indoaniline which precipitates is then filtered, washed with water, recrystallized in a mixture of dimethylformamide and water and dried under a vacuum. It exhibits a melting point of 178° C.

| Analysis | Calculated For $C_{17}H_{18}ClN_3O_2$ | Found |
|---|---|---|
| C% | 61.53 | 61.30 |
| H% | 5.46 | 5.15 |
| N% | 12.66 | 12.38 |
| Cl% | 10.68 | 10.43 |

EXAMPLE XXI

Preparation of N-[(4'-dimethylamino-2'-chloro) phenyl]-6-methyl-3-amino benzoquinoneimine.

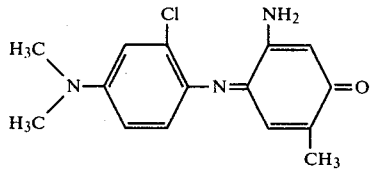

0.01 mole (1.23 g) of 2-methyl-5-amino phenol is dissolved in 10 cc of acetone to which have been added 5 cc of water and 15 cc of ammonia (22° Bé). To the resulting solution, cooled to about +5° C., there are added, little by little, with agitation and simultaneously with the use of a double funnel, 0.01 mole (2.44 g) of the dihydrochloride of 3-chloro-4-amino-N,N-dimethylaniline dissolved in 15 cc of water, and 0.01 mole (2.3 g) of ammonium persulfate dissolved in 10 cc of water. At the end of this addition, the stirring of the reaction mixture is continued for 30 minutes. The above indoaniline which has precipitated in the form of crystals is then filtered, washed with water, recrystallized in a mixture of dimethylformamide and water and dried under a vacuum. It exhibits a melting point of 203° C.

| Analysis | Calculated For $C_{15}H_{16}ClN_3O$ | Found |
|---|---|---|
| C% | 62.16 | 62.33 |
| H% | 5.56 | 5.42 |
| N% | 14.50 | 14.40 |
| Cl% | 12.23 | 12.32 |

EXAMPLE XXII

Preparation of N-[(4'-dimethylamino-2'-methyl) phenyl]-6-methyl-3-acetylamino benzoquinoneimine.

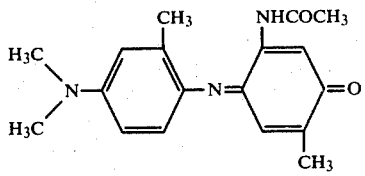

0.01 mole (1.65 g) of 2-methyl-5-acetylamino phenol is dissolved in 20 cc of acetone, 5 cc of water and 15 cc of ammonia (22° Bé). To the resulting solution, maintained at a temperature of about +5° C., there are added, little by little, with agitation and simultaneously with the aid of a double funnel, 0.01 mole (2.23 g) of the dihydrochloride of 3-methyl-4-amino-N,N-dimethyl aniline dissolved in 15 cc of water, and 0.02 mole (4.6 g) of ammonium persulfate dissolved in 20 cc of water. At the end of this addition, the stirring of the reaction mixture is continued for one hour. The above indoaniline which has precipitated in the form of crystals, is filtered, washed with water, recrystallized in a mixture of dimethylformamide and water and dried under a vacuum. It exhibits a melting point of 182° C.

| Analysis | Calculated For $C_{18}H_{21}N_3O_2$ | Found |
|---|---|---|
| C% | 69.43 | 69.13 |
| H% | 6.80 | 6.88 |
| N% | 13.50 | 13.69 |

EXAMPLE XXIII

Preparation of N-[(4'-dimethylamino-2'-methoxy) phenyl]-6-methyl-3-acetylamino benzoquinoneimine.

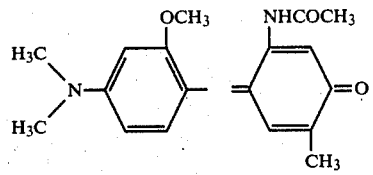

0.01 mole (1.65 g) of 2-methyl-5-acetylamino phenol is dissolved in 50 cc of a 0.6 N NaOh solution. To the resulting solution, cooled to 0° C., there are added, little by little, with agitation and simultaneously with the aid of a double funnel, 0.01 mole (2.64 g) of 3-methoxy-4-amino-N,N-dimethylaniline sulfate dissolved in 20 cc of water, and 0.02 mole (4.6 g) of ammonium persulfate dissolved in 20 cc of water to which have been added 5 cc of ammonia (22° Bé). At the end of this addition, the stirring of the reaction mixture is continued for 15 minutes. The above indoaniline which has precipitated is then filtered, washed with water, recrystallized in a mixture of dimethylformamide and water and dried under a vacuum at 80° C. It exhibits a melting point of 184° C.

| Analysis | Calculated For $C_{18}H_{21}N_3O_3$ | Found |
|---|---|---|
| C% | 66.03 | 65.82 |
| H% | 6.47 | 6.60 |
| N% | 12.84 | 13.02 |

EXAMPLE XXIV

Preparation of N-[(4'-dimethylamino-2'-methoxy) phenyl]-6-methyl-3-carbethoxyamino benzoquinoneimine.

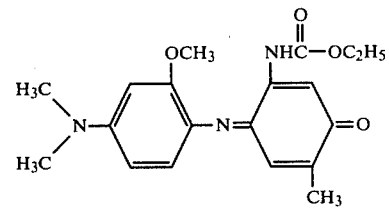

0.02 mole (5.28 g) of 3-methoxy-4-amino-N,N-dimethylaniline sulfate and 0.02 mole (3.9 g) of 2-methyl-5-carbethoxyamino phenol are dissolved in 25 cc of acetone, 50 cc of water and 15 cc of ammonia (22° Bé). To the resulting solution, cooled to about 0° C., there is added, little by little, with agitation, 0.04 mole (9.2 g) of ammonium persulfate dissolved in 40 cc of water. At the end of this addition, stirring of the reaction mixture is continued for 30 minutes. The above indoaniline which has precipitated in the form of crystals is filtered, washed with water, recrystallized in a mixture of dimethylformamide and water and dried under a vacuum at 100° C. It exhibits a melting point of 182° C.

| Analysis | Calculated For $C_{19}H_{23}N_3O_4$ | Found |
|---|---|---|
| C% | 63.85 | 63.88 |
| H% | 6.48 | 6.39 |
| N% | 11.76 | 11.80 |

EXAMPLE XXV

Preparation of N-[(4'-dimethylamino-2'-methyl) phenyl]-2,6-dimethyl-3-amino benzoquinoneimine.

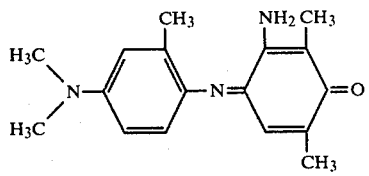

0.02 mole (3.47 g) of the hydrochloride of 2,6-dimethyl-5-amino phenol is dissolved in 40 cc of acetone, 10 cc of water and 30 cc of ammonia (22 Bé). To the resulting solution, maintained at a temperature of about +5° C., there are added, little by little, with agitation and simultaneously with the aid of a double funnel, 0.02 mole (4.46 g) of the dihydrochloride of 3-methyl-4-amino-N,N-dimethylaniline dissolved in 25 cc of water, and 0.02 mole (4.60 g) of ammonium persulfate dissolved in 20 cc of water. At the end of these additions, stirring of the reaction mixture is continued for one hour at ambient temperature. The above indoaniline which has precipitated in the form of crystals is filtered, washed with water, recrystallized in a mixture of dimethylformamide and water and dried under a vacuum. It exhibits a melting point of 170° C.

| Analysis | Calculated For $C_{17}H_{21}N_3O$ | Found |
|---|---|---|
| C% | 72.05 | 71.85 |
| H% | 7.47 | 7.22 |
| N% | 14.83 | 14.90 |

EXAMPLE XXVI

Preparation of N-[(4'-dimethylamino-2'-chloro) phenyl]-2,6-dimethyl-3-amino benzoquinoneimine.

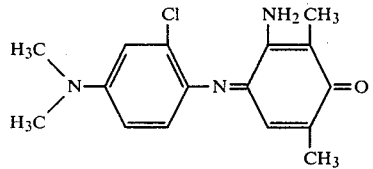

0.02 mole (3.5 g) of the hydrochloride of 2,6-dimethyl-5-amino phenol and 0.022 mole (5.36 g) of the dihydrochloride of 3-chloro-4-amino-N,N-dimethylaniline are dissolved in 50 cc of acetone, 40 cc of water and 40 cc of ammonia (22° Bé). To the resulting solution there are added 100 cc of $H_2O_2$ (20 volumes) and the resulting mixture is left to stand for 6 hours at ambient temperature. The above indoaniline which has precipitated in the form of crystals is then filtered, washed with water and dried under a vacuum. It exhibits a melting point of 183° C.

| Analysis | Calculated For $C_{16}H_{18}ClN_3O$ | Found |
|---|---|---|
| C% | 63.25 | 63.16 |
| H% | 5.97 | 6.00 |
| N% | 13.83 | 13.98 |
| Cl% | 11.67 | 11.79 |

EXAMPLE XXVII

Preparation of N-[(4'-dimethylamino-2'-methoxy) phenyl]-2,6-dimethyl-3-amino benzoquinoneimine.

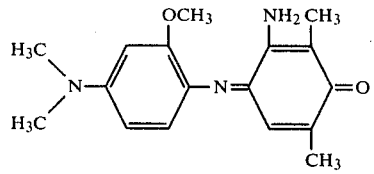

Into 50 cc of a 0.6 N NaOH solution to which have been added 20 cc of ethanol, there are introduced 0.02 mole (3.6 g) of 3-methoxy-4-nitroso-N,N-dimethyl-aniline and 0.022 mole (3.9 g) of the hydrochloride of 2,6-dimethyl-5-amino phenol. The resulting reaction mixture is stirred for one hour at 50° C. The above indoaniline which precipitates is then filtered and washed several times with water at 50° C., and then with acetone. After recrystallization in ethylacetate and drying under a vacuum, it exhibits a melting point of 152° C.

| Analysis | Calculated For $C_{17}H_{21}N_3O_2$ | Found |
|---|---|---|
| C% | 68.20 | 68.09 |
| H% | 7.07 | 7.21 |
| N% | 14.04 | 14.23 |

EXAMPLE XXVIII

Preparation of N-[(4'-dimethylamino-2'-methyl) phenyl]-2,6-dimethyl-3-acetylamino benzoquinoneimine.

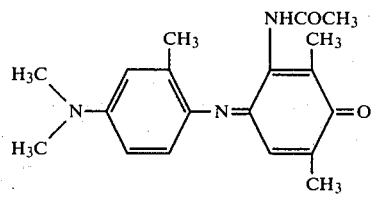

0.01 mole (1.79 g) of 2,6-dimethyl-5-acetylamino phenol is dissolved in 20 cc of acetone, 5 cc of water and 15 cc of ammonia (22° Bé). To the resulting solution, maintained at a temperature of about +5° C., there are added, little by little, with agitation and simultaneously with the aid of a double funnel, 0.01 mole (2.23 g) of the dihydrochloride of 3-methyl-4-amino-N,N-dimethylaniline dissolved in 15 cc of water, and 0.02 mole (4.6 g) of ammonium persulfate dissolved in 20 cc of water. At the end of these additions, the stirring of the reaction mixture is continued for one hour at ambient temperature. The above indoaniline which has precipitated is then filtered, washed with water, recrystallized in a mixture of dimethylformamide and water and dried under a vacuum. It exhibits a melting point of 184° C.

| Analysis | Calculated For $C_{19}H_{23}N_3O_2$ | Found |
|---|---|---|
| C% | 70.13 | 70.00 |
| H% | 7.12 | 7.42 |
| N% | 12.91 | 13.01 |

EXAMPLE XXIX

Preparation of N-[(4'-dimethylamino-2'-chloro) phenyl]-2,6-dimethyl-3-acetylamino benzoquinoneimine.

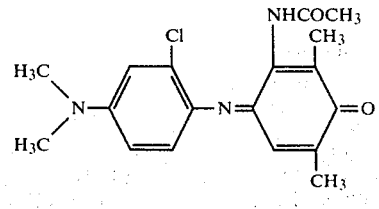

0.01 mole (1.79 g) of 2,6-dimethyl-5-acetylamino phenol and 0.01 mole (2.44 g) of the dihydrochloride of 3-chloro-4-amino-N,N-dimethylaniline are dissolved in 20 cc of acetone, 15 cc of water and 15 cc of ammonia (22° Bé). To the resulting solution, cooled to about +5° C., there is added, little by little, with agitation, 0.02 mole (4.6 g) of ammonium persulate dissolved in 20 cc of water. At the end of this addition, the stirring of the reaction mixture is continued for 30 minutes. The above indoaniline which has precipitated is then filtered, washed with water, recrystallized in a mixture of dimethylformamide and water and dried under a vacuum at 100° C. It exhibits a melting point of 182° C.

| Analysis | Calculated For $C_{18}H_{20}ClN_3O_2$ | Found |
|---|---|---|
| C% | 62.52 | 62.58 |
| H% | 5.83 | 6.00 |
| N% | 12.15 | 12.33 |
| Cl% | 10.25 | 10.00 |

EXAMPLE XXX

Preparation of N-[(4'-dimethylamino-2'-methoxy) phenyl]-2,6-dimethyl-3-acetylamino benzoquinoneimine.

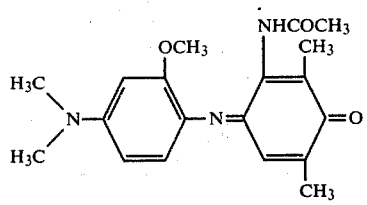

0.01 mole (2.64 g) of 3-methoxy-4-amino-N,N-dimethylaniline sulfate and 0.01 mole (1.8 g) of 2,6-dimethyl-5-acetylamino phenol are dissolved in 25 cc of acetone, 50 cc of water and 15 cc of ammonia (22° Bé). To the resulting solution, maintained at a temperature of about 0° C., there is added, little by little, with agitation, 0.02 mole (4.6 g) of ammonium persulfate dissolved in 20 cc of water. At the end of this addition, the stirring of the reaction mixture is continued for 30 minutes. The above indoanoline which has precipitated is then filtered, washed first with water, then with a little dimethylformamide and finally with water. After drying under a vacuum, the product exhibits a melting point of 186° C.

| Analysis | Calculated For $C_{19}H_{23}N_3O_3$ | Found |
|---|---|---|
| C% | 66.84 | 66.64 |
| H% | 6.79 | 6.70 |
| N% | 12.31 | 12.42 |

EXAMPLE XXXI

Preparation of N-[(4'-dimethylamino-2'-chloro) phenyl]-6-methyl-3-($\beta$-hydroxyethylamino)benzoquinoneimine.

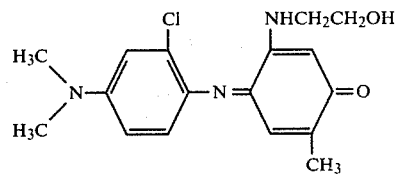

0.01 mole (1.67 g) of 2-methyl-5-(N-$\beta$-hydroxyethylamino) phenol is dissolved in 10 cc of acetone, 5 cc of water and 15 cc of ammonia (22° Bé). To the resulting solution, maintained at a temperature of about +5° C., there are added, little by little, with agitation and simultaneously with the aid of a double funnel, 0.01 mole (2.43 g) of the dihydrochloride of 3-chloro-4-amino-N,N-dimethylaniline dissolved in 15 cc of water, and 0.01 mole (2.3 g) of ammonium persulfate dissolved in 10 cc of water. At the end of these additions, the stirring of the reaction mixture is continued for 30 minutes. The above indoaniline which has precipitated in the form of crystals is then filtered, washed with water, recrystallized in a mixture of dimethylformamide and water and dried under a vacuum. It exhibits a melting point of 176° C.

| Analysis | Calculated For $C_{17}H_{20}N_3O_2Cl$ | Found |
|---|---|---|
| C % | 61.17 | 60.94 |
| H % | 5.99 | 6.10 |
| N % | 12.60 | 12.51 |
| Cl % | 10.65 | 10.60 |

EXAMPLE XXXII

Preparation of N-[(4'-diethylamino-3'-methyl) phenyl]-6-methyl-3-acetylamino benzoquinoneimine.

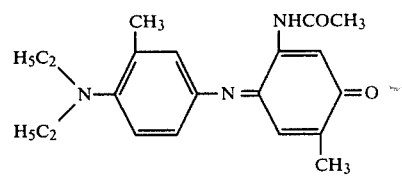

0.0064 mole (1.06 g) of 2-methyl-5-acetylamino phenol and 0.0064 (1.65 g) of 2-methyl-4-amino-N,N-diethyl aniline are dissolved in 80 cc of a 50% hydroacetonic solution to which have been added 20 cc of ammonia (22° Bé). To the resulting solution, cooled to 0° C., there is added, little by little, with a little agitation, 0.0128 mole (2.9 g) of ammonium persulfate dissolved in 20 cc of water. The resulting reaction mixture is left to stand overnight at 0° C. The above indoaniline which forms first as an oil, crystallizes and the resulting crystals are filtered, washed with water and recrystallized in a mixture of dimethylformamide and water. After drying under a vacuum the product exhibits a melting point of 84° C.

| Analysis | Calculated For $C_{20}H_{25}N_3O_2 \cdot O \cdot 5H_2O$ | Found |
|---|---|---|
| C% | 68.94 | 68.97 |
| H% | 7.52 | 7.42 |
| N% | 12.06 | 11.98 |

EXAMPLE XXXIII

Preparation of N-[(4'-dimethylamino-3'-chloro) phenyl]-2,6-dimethyl benzoquinoneimine.

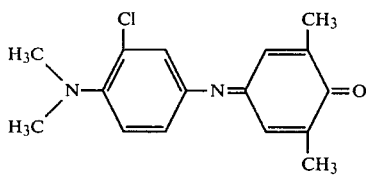

0.01 mole (1.22 g) of 2,6-dimethyl phenol and 0.01 mole (1.70 g) of 2-chloro-4-amino-N,N-dimethylaniline are dissolved in 30 cc of a 50% hydroacetonic solution to which have been added 15 cc of ammonia (22° Bé). To the resulting solution, maintained at a temperature of 0° C., there is added, little by little, with agitation 0.02 mole (4.6 g) of ammonium persulfate dissolved in 20 cc of water. At the end of this addition, the stirring of the reaction mixture is continued for 30 minutes. The above indoaniline which has precipitated in the form of crystals is then filtered, washed with water and recrystallized in a mixture of dimethylformamide and water and dried under a vacuum. It exhibits a melting point of 62° C.

| Analysis | Calculated For $C_{16}H_{17}ClN_2O$ | Found |
|---|---|---|
| C% | 66.19 | 66.39 |
| H% | 5.58 | 5.73 |
| N% | 9.70 | 9.87 |
| Cl% | 12.27 | 12.47 |

EXAMPLE XXXIV

Preparation of N-[(4'-dimethylamino-3'-chloro) phenyl]-6-methyl-3-amino benzoquinoneimine.

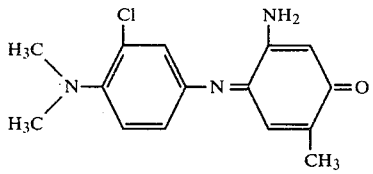

0.004 mole (1.33 g) of N-[(4'-dimethylamino-3'-chloro) phenyl]-6-methyl-3-acetylamino benzoquinoneimine is introduced into 32 cc of a 1 N NaOH solution to which have been added 8 cc of ethylalcohol (95° titer). The resulting reaction mixture is agitated for a period of 24 hours while maintaining the temperature thereof at about 25° C. The above indoaniline which precipitates is then filtered and washed with water. The raw product contains only a trace of the initial reactant (measured by chromatography). After recrystallization of this raw product in a mixture of dimethylformamide and water and washing with acetone it is chromatographically pure. After drying under a vacuum, it exhibits a melting point of 152° C.

| Analysis | Calculated For $C_{15}H_{16}ClN_3O$ | Found |
|---|---|---|
| C% | 62.16 | 62.38 |
| H% | 5.56 | 5.36 |
| N% | 14.50 | 14.57 |
| Cl% | 12.23 | 12.13 |

EXAMPLE XXXV

Preparation of N-[(4'-dimethylamino-3'-chloro) phenyl]-6-chloro-3-amino benzoquinoneimine.

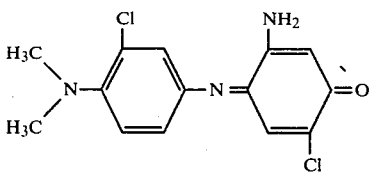

0.01 mole (1.70 g) of 2-chloro-4-amino-N,N-dimethylaniline and 0.01 mole (1.43 g) of 2-chloro-5-amino phenol are dissolved in 20 cc of water, 30 cc of ethylalcohol (95° titer) and 10 cc of ammonia (22° Bé). To the resulting solution, maintained at a temperature of about 0° C., there is added, little by little, with agitation, 0.01 mole (2.3 g) of ammonium persulfate dissolved in 20 cc of water. At the end of this addition, the stirring of the reaction mixture is continued for 30 minutes. The above indoaniline which has precipitated in the form of reddish brown flakes with golden flints is then filtered, washed with water and recrystallized in a mixture of dimethylformamide and water. After drying under a vacuum at 100° C., the product exhibits a melting point of 182° C.

| Analysis | Calculated For $C_{14}H_{13}N_3Cl_2O$ | Found |
|---|---|---|
| C% | 54.19 | 54.19 |
| H% | 4.19 | 4.30 |
| N% | 13.54 | 13.66 |
| Cl% | 12.90 | 23.12 |

EXAMPLE XXXVI

Preparation of N-[(4'-dimethylamino-3'-chloro) phenyl]-2,6-dimethyl-3-amino benzoquinoneimine.

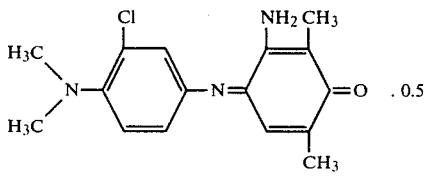

0.02 mole (3.47 g) of the hydrochloride of 2,6-dimethyl-5-amino phenol and 0.02 mole (3.42 g) of 2-chloro-4-amino-N,N-dimethylaniline are dissolved in 120 cc of a 50% hydroacetonic solution to which have been added 30 cc of ammonia (22° Bé). To the resulting solution, maintained at a temperature of 0° C., there is added, little by little, with agitation 0.04 mole (9.2 g) of ammonium persulfate dissolved in 40 cc of water. At the end of this addition, the stirring of the reaction mixture is continued for 30 minutes at 0° C. The above indoaniline which precipitates is then filtered, washed with water and recrystallized in a mixture of dimethylformamide and water. After drying under a vacuum at 60° C., it exhibits a melting point of 137° C.

| Analysis | Calculated For C₁₆H₁₈N₃OCl . O . 5H₂O | Found |
|---|---|---|
| C% | 61.44 | 61.25 |
| H% | 6.08 | 6.16 |
| N% | 13.44 | 13.24 |
| Cl% | 11.36 | 11.31 |

EXAMPLE XXXVII

Preparation of N-[(4'-dimethylamino-3'-chloro) phenyl]-6-methyl-3-acetylamino benzoquinoneimine.

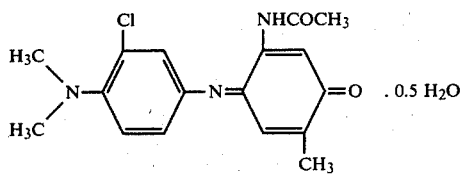

0.01 mole (1.65 g) of 2-methyl-5-acetylamino phenol and 0.01 mole (1.71 g) of 2-chloro-4-amino-N,N-dimethylaniline are dissolved in 60 cc a 50% hydroacetonic solution to which have been added 15 cc of ammonia (22° Bé). To the resulting solution, maintained at a temperature of about 0° C., there is added, little by little, with agitation, 0.02 mole (4.6 g) of ammonium persulfate dissolved in 20 cc of water. At the end of this addition, the stirring of the reaction mixture is continued for 30 minutes. The above indoaniline which has precipitated in the form of crystals is then filtered, washed with water, recrystallized in a mixture of dimethylformamide and water and dried under a vacuum. It exhibits a melting point of 156° C.

| Analysis | Calculated For C₁₇H₁₈O₂N₃Cl . 0.5H₂O | Found |
|---|---|---|
| C % | 59.91 | 59.87 |
| H % | 5.62 | 5.60 |
| N % | 12.33 | 12.58 |
| Cl % | 10.40 | 10.52 |

EXAMPLE XXXVIII

Preparation of N-[(4'-dimethylamino-3'-chloro) phenyl]-2,6-dimethyl-3-acetylamino benzoquinoneimine.

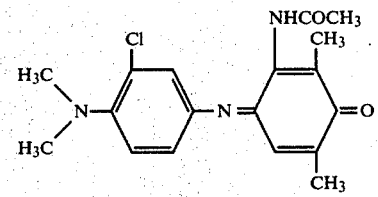

0.2 mole (35.8 g) of 2,6-dimethyl-5-acetylamino phenol and 0.2 mole (34.0 g) of 2-chloro-4-amino-N,N-dimethylaniline are dissolved in 600 cc of a 50% hydroacetonic solution to which have been added 300 cc of ammonia (22° Bé). To the resulting solution, maintained at a temperature of about +5° C., there is added, little by little, with agitation, 0.4 mole (92 g) of ammonium persulfate dissolved in 400 cc of water. At the end of this addition, the stirring of the reaction mixture is continued for 30 minutes. The above indoaniline which has precipitated is then filtered, washed with water, recrystallized in a mixture of dimethylformamide and water and dried under a vacuum. It exhibits a melting point of 136° C.

| Analysis | Calculated For C₁₈H₂₀Cl N₃O₂ | Found |
|---|---|---|
| C% | 62.52 | 62.54 |
| H% | 5.82 | 5.95 |
| N% | 12.15 | 12.24 |
| Cl% | 10.25 | 10.42 |

EXAMPLE XXXIX

Preparation of N-[(4'-dimethylamino-3'-chloro) phenyl]-6-methyl-3-carbethoxyamino benzoquinoneimine.

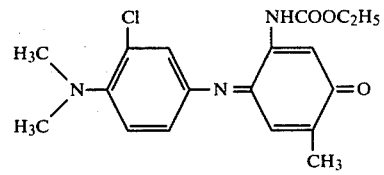

0.1 mole (17 g) of 2-chloro-4-amino-N,N-dimethylaniline and 0.1 mole (19.5 g) of 2-methyl-5-carbethoxyamino phenol are dissolved in 500 cc of ethyl alcohol (95° titer), 250 cc of water and 150 cc of ammonia (22° Bé). To the resulting solution maintained at a temperature of about 0° C., there is added, little by little, with agitation, 0.2 mole (46 g) of ammonium persulfate dissolved in 200 cc of water. At the end of this addition, the stirring of the reaction mixture is continued for one hour. The above indoaniline which has precipitated in the form of crystals is then filtered and washed with a 50% hydroethanolic solution. After recrystallization in a mixture of dimethylformamide and water and drying under a vacuum at 100° C., the product exhibits a melting point of 142° C.

| Analysis | Calculated For C₁₈H₂₀N₃O₃Cl | Found |
|---|---|---|
| C% | 59.75 | 59.81 |
| H% | 5.54 | 5.69 |
| N% | 11.62 | 11.55 |
| Cl% | 9.82 | 9.89 |

EXAMPLES OF USE

Section A - Examples of Hair Setting Lotions

| (a) Dye according to Example IV | 0.02 | g |
|---|---|---|
| Copolymer of vinyl acetate and crotonic acid 90/10; molecular weight 45,000 to 50,000 | 1 | g |
| Isopropyl alcohol | 20 | g |
| Triethanolamine q.s.p. pH 6.5 | | |
| Water q.s.p. | 100 | g |

This composition when applied as a hair setting lotion to bleached hair imparts thereto a purple-ash shade.

| (b) | Dye according to Example VI | 0.15 | g |
| --- | --- | --- | --- |
| | Terpolymer of methylmethacrylate/ stearylmethacrylate/dimethylmethacrylate, 20/23/57 (made in accordance with SN 287,845 filed 11-9-1972) | 2.5 | g |
| | Ethyl alcohol (96°) | 30 | g |
| | Triethanolamine q.s.p. pH 7.5 | | |
| | Water q.s.p. | 100 | g |

This composition when applied as a hair setting lotion to bleached hair imparts thereto a silvery, blue-gray coloration.

| (c) | Dye according to Example VIII | 0.1 | g |
| --- | --- | --- | --- |
| | Polyvinylpyrrolidone - M.W. 40,000 | 2 | g |
| | Isopropyl alcohol | 35 | g |
| | Triethanolamine q.s.p. pH 9 | | |
| | Water q.s.p. | 100 | g |

This composition when applied as a hair setting lotion to bleached hair imparts thereto a chatoyant seagreen coloration.

| (d) | Dye according to Example V | 0.15 | g |
| --- | --- | --- | --- |
| | Copolymer of vinyl acetate/ crotonic acid 90/10, M.W. 45,000 to 50,000 | 1.5 | g |
| | Ethyl alcohol (96°) | 30 | g |
| | Triethanolamine q.s.p. pH 6.2 | | |
| | Water q.s.p. | 100 | g |

This composition when applied as a hair setting lotion to bleached hair imparts thereto a bright blue-green coloration.

| (e) | Dye according to Example XI | 0.12 | g |
| --- | --- | --- | --- |
| | Polyvinylpyrrolidone, M.W. 40,000 | 1 | g |
| | Ethyl alcohol (96°) | 20 | g |
| | Triethanolamine q.s.p. pH 10.2 | | |
| | Water q.s.p. | 100 | g |

This composition when applied as a hair setting lotion to bleached hair imparts thereto a Nordic ash-blond coloration.

| (f) | N-[(4'-dimethylamino) phenyl]-3-acetylamino benzoquinoneimine | 0.2 | g |
| --- | --- | --- | --- |
| | Polyvinylpyrrolidone/vinyl acetate, 70/30, M.W. 40,000 | 3 | g |
| | Ethyl alcohol (96°) | 45 | g |
| | Triethanolamine q.s.p. pH 7.8 | | |
| | Water q.s.p. | 100 | g |

This composition when applied as a hair setting lotion to bleached hair imparts thereto a silvery Prussian blue coloration.

| (g) | Dye according to Example X | 0.04 | g |
| --- | --- | --- | --- |
| | Terpolymer of methylmethacrylate/ stearylmethacrylate/dimethylmethacrylate, 20/23/57 (made in accordance with SN 287,845 filed 11-9-1972) | 3 | g |
| | Ethyl alcohol (96°) | 50 | g |
| | Triethanolamine q.s.p. pH 8.2 | | |
| | Water q.s.p. | 100 | g |

This composition when applied as a hair setting lotion to bleached hair imparts thereto a pale glycine coloration.

| (h) | N-[(4'-dimethylamino) phenyl]-2,6-tert. butyl benzoquinoneimine | 0.05 | g |
| --- | --- | --- | --- |
| | Polyvinylpyrrolidone, M.W. 40,000 | 3 | g |
| | Isopropyl alcohol | 50 | g |
| | Triethanolamine q.s.p. pH 6 | | |
| | Water q.s.p. | 100 | g |

This composition when applied as a hair setting lotion to bleached hair imparts thereto a mauve shade.

| (i) | N-[(4'-dimethylamino) phenyl]-3-methoxy benzoquinoneimine | 0.1 | g |
| --- | --- | --- | --- |
| | Polyvinylpyrrolidone, M.W. 40,000 | 1.5 | g |
| | Ethyl alcohol (96°) | 30 | g |
| | Triethanolamine q.s.p. pH 6 | | |
| | Water q.s.p. | 100 | g |

This composition when applied as a hair setting lotion to bleached hair imparts thereto a light lavender-blue color.

| (j) | Dye according to Example I | 0.08 | g |
| --- | --- | --- | --- |
| | Copolymer of polyvinylpyrrolidone/ vinyl acetate, 60/40 M.W. 80,000-120,000 | 2 | g |
| | Ethyl alcohol (96°) | 25 | g |
| | Triethanolamine q.s.p. pH 8.7 | | |
| | Water q.s.p. | 100 | g |

This composition when applied as a hair setting lotion to bleached hair imparts thereto a pale shade with golden glints.

| (k) | N-[(4'-dimethylamino) phenyl] benzoquinoneimine | 0.12 | g |
| --- | --- | --- | --- |
| | Copolymer of polyvinylpyrrolidone/ vinyl acetate, 60/40, M.W. 80,000-120,000 | 2.5 | g |
| | Isopropyl alcohol | 40 | g |
| | Triethanolamine q.s.p. pH 7.5 | | |
| | Water q.s.p. | 100 | g |

This composition when applied as a hair setting lotion to bleached hair imparts thereto a pale-green coloration with golden glints.

| (l) | Dye according to Example IX | 0.05 | g |
| --- | --- | --- | --- |
| | Copolymer of polyvinylpyrrolidone/ vinyl acetate, 70/30, M.W. 40,000 | 1 | g |
| | Ethyl alcohol (96°) | 50 | g |
| | Triethanolamine q.s.p. pH 6.8 | | |
| | Water q.s.p. | 100 | g |

This composition when applied as a hair setting lotion to bleached hair imparts thereto a bright sea-green coloration.

| (m) | Dye according to Example VII | 0.05 | g |
| --- | --- | --- | --- |
| | Copolymer of polyvinylpyrrolidone/ vinyl acetate, 70/30, M.W. 40,000 | 2 | g |
| | Isopropyl alcohol | 45 | g |
| | Triethanolamine q.s.p. pH 8.5 | | |
| | Water q.s.p. | 100 | g |

This composition when applied as a hair setting lotion to bleached hair imparts thereto a pearly, pale rose shade.

| (n) | Dye according to Example II | 0.1 | g |
|---|---|---|---|
| | Copolymer of polyvinylpyrrolidone/ vinyl acetate, 30/70, M.W. 160,000 | 3 | g |
| | Isopropyl alcohol | 50 | g |
| | Triethanolamine q.s.p. pH 9 | | |
| | Water q.s.p. | 100 | g |

This composition when applied as a hair setting lotion to bleached hair imparts thereto a steel, blue-gray coloration.

| (o) | N-[(4'-dimethylamino) phenyl]-2,5-dimethyl benzoquinoneimine | 0.15 | g |
|---|---|---|---|
| | Copolymer of vinyl acetate/ crotonic acid 90/10, M.W. 45,000 to 50,000 | 1 | g |
| | Ethyl alcohol (96°) | 40 | g |
| | Triethanolamine q.s.p. pH 10 | | |
| | Water q.s.p. | 100 | g |

This composition when applied as a hair setting lotion to bleached hair imparts thereto a steel blue-gray coloration.

| (p) | Dye according to Example III | 0.08 | g |
|---|---|---|---|
| | Copolymer of vinyl acetate/crotonic acid 90/10, M.W. 45,000-50,000 | 1 | g |
| | Ethyl alcohol | 50 | g |
| | Triethanolamine q.s.p. pH 9.5 | | |
| | Water q.s.p. | 100 | g |

This composition when applied as a hair setting lotion to bleached hair imparts thereto an ash-gray coloration.

| (q) | N-[(4'-dimethylamino) phenyl]-2,6-dimethyl benzoquinoneimine | 0.05 | g |
|---|---|---|---|
| | Polyvinylpyrrolidone, M.W. 40,000 | 3 | g |
| | Isopropyl alcohol | 40 | g |
| | Triethanolamine q.s.p. pH 10.2 | | |
| | Water q.s.p. | 100 | g |

This composition when applied as a hair setting lotion to bleached hair imparts thereto a silvery, blue-green coloration.

| (r) | Dye according to Example XII | 0.08 | g |
|---|---|---|---|
| | Copolymer of polyvinylpyrrolidone/ vinyl acetate, 30/70, M.W. 160,000 | 1.5 | g |
| | Ethyl alcohol (96°) | 25 | g |
| | Triethanolamine q.s.p. pH 7.5 | | |
| | Water q.s.p. | 100 | g |

This composition when applied as a hair setting lotion to bleached hair imparts thereto a pearly beige coloration.

| (s) | Dye according to Example XIII | 0.09 | g |
|---|---|---|---|
| | Copolymer of polyvinylpyrrolidone/ vinyl acetate, 70/30, M.W. 40,000 | 1.5 | g |
| | Ethyl alcohol (96°) | 50 | g |
| | Triethanolamine q.s.p. pH 8.5 | | |
| | Water q.s.p. | 100 | g |

This composition when applied as a hair setting lotion to bleached hair imparts thereto, a rose-gray coloration.

| (t) | Dye according to Example XIV | 0.52 | g |
|---|---|---|---|
| | Copolymer of vinyl acetate/ crotonic acid 90/10, M.W. 45,000-50,000 | 2 | g |
| | Ethanol (96°) | 50 | g |
| | Water q.s.p. | 100 | g |
| | Triethanolamine q.s.p. pH 7 | | |

This composition when applied as a hair setting lotion to bleached hair imparts thereto, a light silvery-gray coloration.

| (u) | Dye according to Example XV | 0.04 | g |
|---|---|---|---|
| | Copolymer of polyvinylpyrrolidone/ vinyl acetate, 30/70, M.W. 60,000 | 2 | g |
| | Ethyl alcohol (96°) | 40 | g |
| | Triethanolamine, q.s.p. pH 9 | | |
| | Water q.s.p. | 100 | g |

This composition when applied as a hair setting lotion to bleached hair imparts thereto a light pearly blue coloration.

| (v) | Dye according to Example XVI | 0.2 | g |
|---|---|---|---|
| | Copolymer of polyvinylpyrrolidone/ vinyl acetate, 30/70, M.W. 60,000 | 2 | g |
| | Ethyl alcohol (96°) | 40 | g |
| | Triethanolamine, q.s.p. pH 7 | | |
| | Water q.s.p. | 100 | g |

This composition when applied as a hair setting lotion to bleached hair imparts thereto a lightly violaceous blue coloration.

| (w) | Dye according to Example XVII | 0.0075 | g |
|---|---|---|---|
| | Copolymer of polyvinylpyrrolidone/ vinyl acetate, 60/40, sold under the name of PVP/VA S630 | 2 | g |
| | Isopropanol | 35 | g |
| | Triethanolamine q.s.p. pH 7.5 | | |
| | Water q.s.p. | 100 | g |

This composition when applied as a hair setting lotion to bleached hair imparts thereto a light pearly turquoise blue coloration.

| (x) | Dye according to Example XVIII | 0.25 | g |
|---|---|---|---|
| | Copolymer of vinyl acetate/ crotonic acid, 90/10, M.W. - 45,000 to 50,000 | 2 | g |
| | Ethyl alcohol (96°) | 50 | g |
| | Triethanolamine q.s.p. pH 7 | | |
| | Water q.s.p. | 100 | g |

This composition when applied as a hair setting lotion to bleached hair imparts thereto an intense violet coloration.

| (y) | Dye according to Example XIX | 0.6 | g |
|---|---|---|---|
| | Copolymer of vinyl acetate/ crotonic acid, 90/10, M.W. 45,000 to 50,000 | 1 | g |
| | Ethyl alcohol (96°) | 36 | g |
| | Triethanolamine q.s.p. pH 9 | | |

-continued

| | | | |
|---|---|---|---|
| | Water q.s.p. | 100 | g |

This composition when applied as a hair setting lotion to bleached hair imparts thereto a very luminous parme coloration.

| (z) | Dye according to Example XX | 0.26 | g |
|---|---|---|---|
| | Copolymer of vinyl acetate/ crotonic acid, 90/10, M.W. 45,000 to 50,000 | 2 | g |
| | Ethyl alcohol (96°) | 50 | g |
| | Lactic acid-10% solution, q.s.p. pH 4.5 | | |
| | Water q.s.p. | 100 | g |

This composition when applied as a hair setting lotion to bleached hair imparts thereto a very silvery light violet coloration.

| (aa) | Dye of Example XXI | 0.1 | g |
|---|---|---|---|
| | Copolymer of polyvinylpyrrolidone/ vinyl acetate, 30/70, sold under the name PVP/VAE E335 | 2 | g |
| | Ethyl alcohol (96°) | 40 | g |
| | Ammonia (22°Be), q.s.p. pH 6 | | |
| | Water q.s.p. | 100 | g |

This composition when applied as a hair setting lotion to bleached hair imparts thereto a pearly rose beige coloration.

| (ab) | Dye of Example XXII | 0.15 | g |
|---|---|---|---|
| | Copolymer of polyvinylpyrrolidone/ vinyl acetate, 60/40, sold under the name PVP/VA S630 | 2 | g |
| | Isopropanol | 35 | g |
| | Triethanolamine, q.s.p. pH 9.5 | | |
| | Water q.s.p. | 100 | g |

This composition when applied as a hair setting lotion to bleached hair imparts thereto a pearly light blue coloration

| (ac) | Dye of Example XXIII | 0.1 | g |
|---|---|---|---|
| | Copolymer of polyvinylpyrrolidone/ vinyl acetate, 60/40, sold under the name PVP/VA S630 | 2 | g |
| | Isopropanol | 35 | g |
| | Triethanolamine q.s.p. pH 8.5 | | |
| | Water q.s.p. | 100 | g |

This composition when applied as a hair setting lotion to bleached hair imparts thereto a light blue coloration

| (ad) | Dye of Example XXIV | 0.05 | g |
|---|---|---|---|
| | Copolymer of polyvinylpyrrolidone/ vinyl acetate, 30/70, sold under the name PVP/VAE E335 | 2 | g |
| | Ethyl alcohol (96°) | 40 | g |
| | Lactic acid - 10% solution, q.s.p. pH 5 | | |
| | Water q.s.p. | 100 | g |

This composition when applied as a hair setting lotion to bleached hair imparts thereto a silvery light blue-gray coloration.

| (ae) | Dye of Example XXV | 0.15 | g |
|---|---|---|---|
| | Copolymer of vinyl acetate/ crotonic acid, 90/10, M.W. - 45,000 to 50,000 | 1 | g |
| | Ethyl alcohol (96°) | 36 | g |
| | Lactic acid - 10% solution, q.s.p. pH 5 | | |
| | Water q.s.p. | 100 | g |

This composition when applied as a hair setting lotion to bleached hair imparts thereto a silvery glycine coloration.

| (af) | Dye of Example XXVI | 0.05 | g |
|---|---|---|---|
| | Copolymer of vinyl acetate/ crotonic acid, 90/10, M.W. - 45,000 to 50,000 | 2 | g |
| | Ethyl alcohol (96°) | 50 | g |
| | Triethanolamine q.s.p. pH 5 | | |
| | Water q.s.p. | 100 | g |

This composition when applied as a hair setting lotion to bleached hair imparts thereto a golden-rose coloration.

| (ag) | Dye of Example XXVII | 0.12 | g |
|---|---|---|---|
| | Copolymer of polyvinylpyrrolidone/ vinyl acetate, 30/70, sold under the name PVP/VAE E335 | 2 | g |
| | Ethyl alcohol (96°) | 40 | g |
| | Ammonia (22°Bé), q.s.p. pH 9 | | |
| | Water q.s.p. | 100 | g |

This composition when applied as a hair setting lotion to bleached hair imparts thereto a very luminous parme coloration.

| (ah) | Dye of Example XXVIII | 0.12 | g |
|---|---|---|---|
| | Copolymer of polyvinylpyrrolidone/ vinyl acetate, 60/40, sold under the name PVP/VA S630 | 2 | g |
| | Isopropanol | 35 | g |
| | Ammonia (22°Bé), q.s.p. pH 9 | | |
| | Water q.s.p. | 100 | g |

This composition when applied as a hair setting lotion to bleached hair imparts thereto a myosotis coloration.

| (ai) | Dye of Example XXIX | 0.05 | g |
|---|---|---|---|
| | Copolymer of vinyl acetate/ crotonic acid, 90/10, M.W. - 45,000 to 50,000 | 2 | g |
| | Ethyl alcohol (96°) | 50 | g |
| | Ammonia (22°Bé) q.s.p. pH 8.5 | | |
| | Water q.s.p. | 100 | g |

This composition when applied as a hair setting lotion to bleached hair imparts thereto a silver-gray coloration with violet glints.

| (aj) | Dye of Example XXX | 0.2 | g |
|---|---|---|---|
| | Copolymer of polyvinylpyrrolidone/ vinyl acetate, 60/40, sold under the name PVP/VA S630 | 2 | g |
| | Isopropanol | 35 | g |
| | Lactic acid - 10% solution, q.s.p. pH 5 | | |

-continued

| | | |
|---|---|---|
| Water q.s.p. | 100 | g |

This composition when applied as a hair setting lotion to bleached hair imparts thereto a intense French blue coloration.

| | | | |
|---|---|---|---|
| (ak) | Dye of Example XXXI | 0.05 | g |
| | Copolymer of vinyl acetate/ crotonic acid, 90/10, M.W. - 45,000 to 50,000 | 2 | g |
| | Ethyl alcohol (96°) | 50 | g |
| | Triethanolamine q.s.p. pH 6 | | |
| | Water q.s.p. | 100 | g |

This composition when applied as a hair setting lotion to bleached hair imparts thereto a pearly dog-rose coloration.

| | | | |
|---|---|---|---|
| (al) | Dye of Example XXXI | 0.25 | g |
| | N-[(4'-hydroxy-3'-chloro) phenyl]-2-methyl-5-β-hydroxyethylamino benzoquinoneimine | 0.25 | g |
| | Copolymer of vinyl acetate/ crotonic acid, 90/10, M.W. - 45,000 to 50,000 | 2 | g |
| | Ethyl alcohol (96°) | 36 | g |
| | Ammonia (22°Bé) q.s.p. pH 8 | | |
| | Water q.s.p. | 100 | g |

This composition when applied as a hair setting lotion to bleached hair imparts thereto a rose beige coloration with golden glints.

| | | | |
|---|---|---|---|
| (am) | Dye of Example XIX | 0.12 | g |
| | Dye of Example XVII | 0.05 | g |
| | N-[(4'-hydroxy-3'-chloro) phenyl]-2,6-dimethyl-5-amino benzoquinoneimine | 0.35 | g |
| | Nitroorthophenylenediamine | 0.02 | g |
| | Terpolymer of methylmethacrylate/ stearylmethacrylate/dimethyl-methacrylate, 20/23/57 (made in accordance with SN 287,845 filed 11-9-1972) | 1.25 | g |
| | Ethyl alcohol (96°) | 15 | g |
| | Ammonia (22°Bé) q.s.p. pH 9 | | |
| | Water q.s.p. | 100 | g |

This composition when applied as a hair setting lotion to bleached hair imparts thereto an ash gray coloration.

| | | | |
|---|---|---|---|
| (an) | Dye of Example XVIII | 0.2 | g |
| | N-[(4'-hydroxy) phenyl ]-2-methyl-5-β-hydroxyethylamino benzo-quinoneimine | 0.30 | g |
| | N-[(4'-hydroxy) phenyl ]-2-methyl-5-carbethoxyamino benzoquinone-imine | 0.20 | g |
| | Polyvinylpyrrolidone, M.W. 160,000 | 2 | g |
| | Isopropanol | 25 | g |
| | Ammonia (22° Bé) q.s.p. pH 9.7 | | |
| | Water q.s.p. | 100 | g |

This composition when applied as a hair setting lotion to bleached hair imparts thereto a mahogany coloration.

| | | | |
|---|---|---|---|
| (ao) | Dye of Example XXXII | 0.5 | g |
| | Copolymer of vinyl acetate/ crotonic acid, 90/10, M.W. 45,000 to 50,000 | 2 | g |
| | Ethyl alcohol (96°) | 50 | g |
| | Lactic acid - 10% solution, q.s.p. pH 5 | | |
| | Water q.s.p. | 100 | g |

This composition when applied as a hair setting lotion to bleached hair imparts thereto a tamarisk rose coloration.

| | | | |
|---|---|---|---|
| (ap) | Dye of Example XXXIII | 0.025 | g |
| | Copolymer of vinyl acetate/ crotonic acid, 90/10, M.W. 45,000 to 50,000 | 2 | g |
| | Ethyl alcohol (96°) | 50 | g |
| | Triethanolamine q.s.p. pH 7.5 | | |
| | Water q.s.p. | 100 | g |

This composition when applied as a hair setting lotion to bleached hair imparts thereto a pink champagne coloration.

| | | | |
|---|---|---|---|
| (aq) | Dye of Example XXXIV | 0.040 | g |
| | Copolymer of vinyl acetate/ crotonic acid, 90/10, M.W. 45,000 to 50,000 | 2 | g |
| | Ethyl alcohol (96°) | 50 | g |
| | Triethanolamine q.s.p. pH 7 | | |
| | Water q.s.p. | 100 | g |

This composition when applied as a hair setting lotion to bleached hair imparts thereto a light yellow-orange coloration.

| | | | |
|---|---|---|---|
| (ar) | Dye of Example XXXV | 0.08 | g |
| | Polyvinylpyrrolidone, M.W. 160,000 | 1.5 | g |
| | Ethyl alcohol (96°) | 50 | g |
| | Ammonia (22° Bé) q.s.p. pH 10 | | |
| | Water q.s.p. | 100 | g |

This composition when applied as a hair setting lotion to bleached hair imparts thereto a pearly rose beige coloration.

| | | | |
|---|---|---|---|
| (as) | Dye of Example XXXVI | 0.2 | g |
| | Copolymer of vinyl acetate/ crotonic acid, 90/10, M.W. 45,000 to 50,000 | 1 | g |
| | Ethyl alcohol (96°) | 36 | g |
| | Ammonia (22° Bé) q.s.p. pH 6 | | |
| | Water q.s.p. | 100 | g |

This composition when applied as a hair setting lotion to bleached hair imparts thereto a light orange coloration.

| | | | |
|---|---|---|---|
| (at) | Dye of Example XXXVII | 0.1 | g |
| | Copolymer of vinyl acetate/ crotonic acid, 90/10, M.W. 45,000 to 50,000 | 2 | g |
| | Ethyl alcohol (96°) | 50 | g |
| | Triethanolamine q.s.p. pH 7 | | |
| | Water q.s.p. | 100 | g |

This composition when applied as a hair setting lotion to bleached hair imparts thereto a very luminous light salmon coloration.

| (au) | Dye of Example XXXVIII | 0.5 g |
|---|---|---|
| | Copolymer of polyvinylpyrrolidone/ | |
| | vinyl acetate, 30/70, sold under | |
| | the name PVP/VAE E335 | 2 g |
| | Ethyl alcohol (96°) | 40 g |
| | Triethanolamine q.s.p. pH 9 | |
| | Water q.s.p. | 100 g |

This composition when applied as a hair setting lotion to bleached hair imparts thereto a salmon rose coloration.

| (av) | Dye of Example XXXIX | 0.075 g |
|---|---|---|
| | Copolymer of polyvinylpyrrolidone/ | |
| | vinyl acetate, 30/70, sold under | |
| | the name PVP/VAE E335 | 2 g |
| | Ethyl alcohol (96°) | 40 g |
| | Lactic acid - 10% solution, | |
| | q.s.p. pH 5 | |
| | Water q.s.p. | 100 g |

This composition when applied as a hair setting lotion to bleached hair imparts thereto a golden sand coloration with light pink glints.

| (aw) | Dye of Example XXXVII | 0.10 g |
|---|---|---|
| | Dye of Example XXXVI | 0.12 g |
| | N-[(4'-amino-2'-methoxy-3',5'-dimethyl) phenyl]-2,6-dimethyl-3-acetylamino benzoquinoneimine | 0.05 g |
| | 2-N,N-(methyl,β-hydroxyethyl)amino-5-(4'-amino) anilino-1,4-benzoquinone | 0.08 g |
| | Copolymer of vinyl acetate/ crotonic acid, 90/10, M.W. 45,000 to 50,000 | 2 g |
| | Ethyl alcohol (96°) | 50 g |
| | Ammonia (22° Bé) q.s.p. pH 10 | |
| | Water q.s.p. | 100 g |

This composition when applied as a hair setting lotion to bleached hair imparts thereto an ash beige coloration.

| (ax) | Dye of Example XXXVI | 0.20 g |
|---|---|---|
| | N-[(4'-amino-2'-methoxy-3'-5'-dimethyl) phenyl]-2,6-dimethyl-3-acetylamino benzoquinoneimine | 0.04 g |
| | N-[(4'-(ethyl,β-mesylaminoethyl) amino-2'-methyl) phenyl]-2,3-dimethyl benzoquinoneimine | 0.25 g |
| | Copolymer of vinyl acetate/ crotonic acid, 90/10, M.W. 45,000 to 50,000 | 2 g |
| | Ethanol (95°) | 50 g |
| | Triethanolamine q.s.p. pH 6 | |
| | Water q.s.p. | 100 g |

This composition when applied as a hair setting lotion to 95% naturally white hair, imparts thereto a metallic gray coloration with violet glints.

Section B - Examples of Dye Compositions

| (a) | N-[(4'-dimethylamino) phenyl]-3-acetylamino benzoquinoneimine | 0.3 g |
|---|---|---|
| | Ammonium lauryl sulfate | 20 g |
| | Triethanolamine q.s.p. pH 8.5 | |
| | Water q.s.p. | 100 g |

This dye composition is applied for a period of thirty minutes to white hair at ambient temperature. The hair is then rinsed, shampooed, rinsed again and then dried. A pearly sea-green coloration is thus imparted to the hair.

| (b) | Dye according to Example V | 0.2 g |
|---|---|---|
| | Ammonium lauryl sulfate | 20 g |
| | Triethanolamine q.s.p. pH 9 | |
| | Water q.s.p. | 100 g |

This dye composition is applied for a period of thirty minutes to white hair at ambient temperature. The hair is then rinsed, shampooed, rinsed again and dried. A sea-green coloration is thus imparted to the hair.

| (c) | Dye according to Example VI | 0.3 g |
|---|---|---|
| | Butylglycol | 5 g |
| | Lauryl alcohol oxyethylenated with 10.5 moles of ethylene oxide | 5 g |
| | Triethanolamine q.s.p. pH 9 | |
| | Water q.s.p. | 100 g |

This dye composition is applied to white hair for a period of thirty minutes at ambient temperature. After rinsing, shampooing, rinsing again and drying, a lavender-blue coloration is imparted to the hair.

| (d) | N-[(4'-dimethylamino) phenyl]-3-acetylamino benzoquinoneimine | 0.3 g |
|---|---|---|
| | Ethanol (96°) | 30 g |
| | Acetic acid q.s.p. pH 5 | |
| | Water q.s.p. | 100 g |

This dye composition is applied for about thirty minutes to previously bleached hair. At the end of this period, the hair is rinsed and dried. A brilliant turquoise coloration is thus imparted to the hair.

| (e) | Dye of Example XVII | 0.15 g |
|---|---|---|
| | Diethanolamides of the fatty acids of coprah | 10 g |
| | Phosphoric acid - 10% solution, q.s.p. pH 4 | |
| | Water q.s.p. | 100 g |

This dye composition is applied for a period of twenty minutes at 35° C., to bleached hair and after rinsing, shampooing, and rinsing again imparts thereto a turquoise blue coloration.

| (f) | Dye of Example XIX | 2 g |
|---|---|---|
| | Diethanolamides of fatty acids of coprah | 10 g |
| | Ammonia (22° Bé) q.s.p. pH 10 | |
| | Water q.s.p. | 100 g |

This dye composition is applied for a period of twenty-five minutes to 90% naturally white hair at 35° C., and after rinsing, shampooing and rinsing again imparts thereto a blue gray coloration.

| (g) | Dye of Example XX | 0.3 g |
| --- | --- | --- |
| | Sodium lauryl sulfate with 19% of the starting alcohol being oxyethylenated | 20 g |
| | Ethylenediamine tetraacetic acid- "TRILON B" | 0.2 g |
| | Ammonia (22° Bé) q.s.p. pH 11 | |
| | Water q.s.p. | 100 g |

This dye composition is applied for a period of twenty minutes at 30° C., to bleached hair and after rinsing, shampooing and rinsing again, imparts thereto a light silver coloration with mauve glints.

| (h) | Dye of Example XXI | 0.2 g |
| --- | --- | --- |
| | Monomethyl ester of diethylene glycol | 10 g |
| | Ammonia (22° Bé) q.s.p. pH 9 | |
| | Water q.s.p. | 100 g |

This dye composition is applied for a period of thirty minutes at 25° C., to bleached hair and after rinsing, shampooing and rinsing again imparts thereto a golden rose coloration.

| (i) | Dye of Example XXIII | 0.1 g |
| --- | --- | --- |
| | Ammonium lauryl sulfate | 10 g |
| | acetic acid - 5% solution, q.s.p. pH 7 | |
| | Water q.s.p. | 100 g |

This dye composition is applied for a period of twenty-five minutes at 35° C., to bleached hair and after rinsing, shampooing and rinsing again, imparts thereto a pearly light turquoise coloration.

| (j) | Dye of Example XXIV | 0.25 g |
| --- | --- | --- |
| | Carboxymethyl cellulose | 5 g |
| | Ammonia (22° Bé) q.s.p. pH 11 | |
| | Water q.s.p. | 100 g |

This dye composition is applied for a period of twenty-five minutes at 35° C., to bleached hair and after rinsing, shampooing and rinsing again, imparts thereto a light silver coloration with bluish glints.

| (k) | Dye of Example XXVII | 0.3 g |
| --- | --- | --- |
| | Butyglycol | 5 g |
| | Lauryl alcohol oxyethylenated with 10.5 moles of ethylene oxide | 5 g |
| | Ammonia (22° Bé) q.s.p. pH 10 | |
| | Water q.s.p. | 100 g |

This dye composition is applied for a period of twenty-five minutes at 35° C., to 95% naturally white hair and after rinsing, shampooing and rinsing again, imparts thereto a silver gray coloration with mauve glints.

| (l) | Dye of Example XXX | 0.20 g |
| --- | --- | --- |
| | Carboxymethyl cellulose | 5 g |
| | Ammonia (22° Bé) q.s.p. pH 8 | |
| | Water q.s.p. | 100 g |

This dye composition is applied for a period of twenty-five minutes at 20° C., to bleached hair and after rinsing, shampooing and rinsing again, imparts thereto a silvery light blue coloration.

| (m) | Dye of Example XXVII | 0.30 g |
| --- | --- | --- |
| | N-[(4'-hydroxy-2'-chloro) phenyl]-2-methyl-5-amino benzoquinoneimine | 0.40 g |
| | Ethyl alcohol (96°) | 20 g |
| | Diethanolamides of fatty acids of coprah | 8 g |
| | Ammonia (22° Bé) q.s.p. pH 9.3 | |
| | Water q.s.p. | 100 g |

This dye composition is applied for a period of twenty minutes at ambient temperature to bleached hair and after rinsing, shampooing and rinsing again, imparts thereto a light golden blond coloration with pink glints.

| (n) | Dye of Example XXXIII | 0.75 g |
| --- | --- | --- |
| | Butylglycol | 5 g |
| | Lauryl alcohol oxyethylenated with 10.5 moles of ethylene oxide | 5 g |
| | Ammonia (22° Bé) q.s.p. pH 10.5 | |
| | Water q.s.p. | 100 g |

This dye composition is applied for a period of twenty minutes at ambient temperature to bleached hair and after rinsing, shampooing and rinsing again, imparts thereto a pale golden pink coloration.

| (o) | Dye of Example XXXVI | 0.1 g |
| --- | --- | --- |
| | Lauryl alcohol oxyethylenated with 10.5 moles of ethylene oxide | 5 g |
| | Ammonia (22° Bé) q.s.p. pH 10 | |
| | Water q.s.p. | 100 g |

This dye composition is applied for a period of twenty minutes at 35° C., to bleached hair and after rinsing, shampooing and rinsing again, imparts thereto a very luminous orange coloration.

| (p) | Dye of Example XXXVII | 0.1 g |
| --- | --- | --- |
| | Monomethyl ester of diethylene glycol | 10 g |
| | Ammonia (22° Bé) q.s.p. pH 11 | |
| | Water q.s.p. | 100 g |

This dye composition is applied for a period of twenty-five minutes at 35° C., to bleached hair and after rinsing, shampooing and rinsing again, imparts thereto a pink beige coloration.

| (q) | Dye of Example XXXVIII | 0.25 g |
| --- | --- | --- |
| | Ethyl alcohol (96°) | 20 g |
| | Carboxymethyl cellulose | 5 g |
| | Lactic acid - 10% solution, q.s.p. pH 5 | |
| | Water q.s.p. | 100 g |

This dye composition is applied for a period of ten minutes at 35° C., to bleached hair and after rinsing, shampooing and rinsing again, imparts thereto a tamarisk-pink coloration.

| (r) | Dye of Example XXXIV | 0.425 g |
| --- | --- | --- |
| | Butylglycol | 5 g |
| | Lauryl alcohol oxyethylenated | |

| | | |
|---|---|---|
| | with 10.5 moles of ethylene oxide | 5 g |
| | Ammonia (22° Bé) q.s.p. pH 9 | |
| | Water q.s.p. | 100 g |

This dye composition is applied for a period of twenty minutes at ambient temperature to bleached hair and imparts thereto a pearly golden sand coloration.

| | | |
|---|---|---|
| (s) | Dye of example XXXIII | 0.40 g |
| | Dye of Example XXXIX | 0.80 g |
| | N-[(4'-dimethylamino-2'-methoxy) phenyl]-2,6-dimethyl-3-acetyl-amino benzoquinoneimine | 0.15 g |
| | Diethanolamides of fatty acids of coprah | 10 g |
| | Ammonia (22° Bé) q.s.p. pH 9,7 | |
| | Water q.s.p. | 100 g |

This dye composition is applied for a period of twenty minutes at ambient temperature to bleached hair and imparts thereto a dove gray coloration.

Section C–Examples of Dye Compositions Containing the Indoanilines of Formula (I) and Other Dyes

| | | |
|---|---|---|
| (a) | N-[(4'-dimethylamino) phenyl]-3-acetylamino benzoquinoneimine | 0.2 g |
| | Dihydrochloride of 3-nitro-4-N-(methyl-β-diethylaminoethyl)-amino aniline | 0.1 g |
| | Ammonium lauryl sulfate | 20 g |
| | Triethanolamine q.s.p. pH 8.5 | |
| | Water q.s.p. | 100 g |

This dye composition is applied to white hair for a period of thirty minutes at ambient temperature. After rinsing, shampooing, rinsing again and drying, the hair exhibits a linden coloration with golden glints.

| | | |
|---|---|---|
| (b) | N-[(4'-dimethylamino) phenyl]-2,6-dimethyl benzoquinoneimine | 0.25 g |
| | 2,4,6-trihydroxy-azo benzene | 0.2 g |
| | Ammonium lauryl sulfate | 20 g |
| | Triethanolamine q.s.p. pH 8.2 | |
| | Water q.s.p. | 100 g |

This dye composition is applied to white hair for a period of thirty minutes at ambient temperature. After rinsing, shampooing, rinsing again and drying, the hair exhibits a canary yellow coloration.

| | | |
|---|---|---|
| (c) | N-[(4'-dimethylamino) phenyl]-2,5-dimethyl benzoquinoneimine | 0.3 g |
| | 2-amino-4,4'-dihydroxy-azo benzene | 0.2 g |
| | Ammonium lauryl sulfate | 20 g |
| | Triethanolamine q.s.p. pH 8.8 | |
| | Water q.s.p. | 100 g |

This dye composition is applied to white hair for a period of about thirty minutes at ambient temperature. After rinsing, shampooing, rinsing again and drying, the hair exhibits a yellow-green coloration.

| | | |
|---|---|---|
| (d) | N-[(4'-dimethylamino) phenyl] benzoquinoneimine | 0.2 g |
| | 1,4-di-(β-morpholinoethyl) amino anthraquinone | 0.3 g |
| | Butylglycol | 5 g |
| | Lauryl alcohol, oxyethylenated with 10.5 moles of ethylene oxide | 5 g |
| | Triethanolamine q.s.p. pH 8.5 | |
| | Water q.s.p. | 100 g |

This dye composition is applied to white hair for a period of thirty minutes at ambient temperature. After rinsing, shampooing, rinsing again and drying, the hair exhibits a brilliant lavender-blue coloration.

| | | |
|---|---|---|
| (e) | N-[(4'-dimethylamino) phenyl]-2,6-dimethyl-3-amino benzoquinoneimine | 0.2 g |
| | N-[(4'-amino-2'-methoxy-5'-methyl) phenyl]-3-ureido benzoquinoneimine | 0.1 g |
| | Butylglycol | 5 g |
| | Lauryl alcohol oxyethylenated with 10.5 moles of ethylene oxide | 5 g |
| | Triethanolamine q.s.p. pH 8.6 | |
| | Water q.s.p. | 100 g |

This dye composition is applied to white hair for a period of about thirty minutes at ambient temperature. After rinsing, shampooing, rinsing again and drying, the hair exhibits a gray-green coloration.

| | | |
|---|---|---|
| (f) | Dye according to Example IX | 0.2 g |
| | N-[(4'-amino) phenyl]-2-6-dimethyl-3-ureido benzoquinoneimine | 0.1 g |
| | N-[(4'-amino) phenyl]-2-methyl-5-ureido benzoquinoneimine | 0.1 g |
| | Butylglycol | 5 g |
| | Lauryl alcohol oxyethylenated with 10.5 moles of ethylene oxide | 5 g |
| | Triethanolamine q.s.p. pH 9 | |
| | Water q.s.p. | 100 g |

This dye composition is applied to white hair for a period of about thirty minutes at ambient temperature. After rinsing, shampooing, rinsing again and drying, the hair exhibits a parme shade.

| | | |
|---|---|---|
| (g) | N-[(4'-dimethylamino) phenyl]-2,6-ditertiobutyl benzoquinoneimine | 0.1 g |
| | N-[(4'-hydroxy-3'-chloro) phenyl]-2-chloro-5-amino benzoquinoneimine | 0.1 g |
| | N-[(4'-dimethylamino) phenyl]-3-acetylamino benzoquinoneimine-N',N'-dimethyl iminium chloride | 0.1 g |
| | 5,6-dihydroxy indole | 0.05 g |
| | Butylglycol | 5 g |
| | Lauryl alcohol oxyethylenated with 10.5 moles of ethylene oxide | 5 g |
| | Ammonia q.s.p. pH 11 | |
| | Water q.s.p. | 100 g |

This composition is applied to white hair for a period of about thirty minutes. At the end of this period, the hair is rinsed, washed with water, rinsed again and dried. There is thus imparted to the hair a silvery-seal coloration.

What is claimed is:

1. A process for dyeing keratinic fibers comprising (1) impregnating said fibers with an effective amount of a dye composition for said keratinic fibers, said dye composition comprising an aqueous or hydroalcoholic solution of an indoaniline of the formula

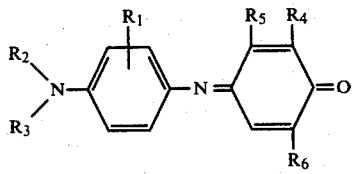

wherein
- $R_1$ is alkyl, halogen or alkoxy,
- $R_2$ and $R_3$ are each alkyl,
- $R_4$ is alkyl,
- $R_5$ is hydrogen, and
- $R_6$ is alkyl or acetylamino, or a tautomeric form thereof, the said alkyl and alkoxy groups containing 1-6 carbon atoms and the said indoaniline being present in an amount of 0.0075 to 2 percent by weight of said composition so as to color said fibers, permitting said composition to remain in contact with said fibers for a period of time ranging from about 5 to 30 minutes and rinsing said fibers.

2. The process of claim 1 which includes washing and drying said dyed and rinsed fibers.

3. The process of claim 1 wherein said indoaniline is selected from the group consisting of
   (1) N-[(4'-diethylamino-2'-methyl)phenyl]2,6-dimethyl benzoquinoeimine,
   (2) N-[(4'-diethylamino-2'-chloro)phenyl]2-acetylamino benzoquinoneimine,
   (3) N-[(4'-dimethylamino-2'-methyl)phneyl]-2,6-dimethyl benzoquinoneimine,
   (4) N-[(4'-dimethylamino-2'-chloro)phenyl]-2,6-dimethyl benzoquinoneimine,
   (5) N-[(4'-dimethylamino-2'-methoxy)phenyl]-2,6-dimethyl benzoquinoneimine, and
   (6) N-[(4'-dimethylamino-3'-chloro)phenyl'-2,6-dimethyl benzoquinoneimine.

4. A process for coloring and setting hair comprising applying to previously wet hair an effective amount of a dye composition comprising a hydroalcoholic solution of an indoaniline of the formula

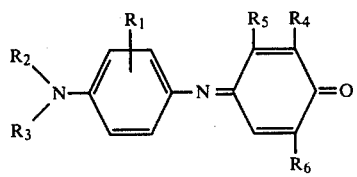

wherein
- $R_1$ is alkyl, halogen or alkoxy,
- $R_2$ and $R_3$ are each alkyl,
- $R_4$ is alkyl,
- $R_5$ is hydrogen, and
- $R_6$ is alkyl or acetylamino, or a tautomeric form thereof, the said alkyl and alkoxy groups containing 1-6 carbon atoms, said composition containing 0.0075 to 2 percent by weight of said indoaniline and also containing an effective amount of a cosmetic film-forming resin and setting said hair.

5. The process of claim 4 wherein said cosmetic film-forming resin is present in an amount of 1 to 3 percent by weight of said composition.

6. The process of claim 4 wherein the alcohol of said hydroalcoholic solution is ethanol or isopropanol, said alcohol being present in an amount of about 20 to 70 percent by weight of said composition.

7. The process of claim 4 which includes wetting the hair prior to applying said dye composition thereto.

8. The process of claim 7 wherein wetting said hair comprises washing and rinsing the hair.

9. The process of claim 7 wherein setting said hair comprises rolling the hair on rollers and then drying said hair.

* * * * *